US011633277B2

(12) United States Patent
Karalnik et al.

(10) Patent No.: US 11,633,277 B2
(45) Date of Patent: Apr. 25, 2023

(54) TEMPERATURE-CONTROL DURING CRIMPING OF AN IMPLANT

(71) Applicant: CARDIOVALVE LTD., Or Yehuda (IL)

(72) Inventors: Maxim Karalnik, Karmiel (IL); Or Cohen, Tel Aviv (IL); Michael Albitov, Kiryat Ono (IL); Oren Shua, Elishama (IL); Meni Iamberger, Kfar Saba (IL); Ilia Hariton, Zichron Yaakov (IL)

(73) Assignee: CARDIOVALVE LTD., Or Yehuda (IL)

( * ) Notice: Subject to any disclaimer, the term of this patent is extended or adjusted under 35 U.S.C. 154(b) by 283 days.

(21) Appl. No.: 16/760,147

(22) PCT Filed: Oct. 21, 2018

(86) PCT No.: PCT/IL2018/051122
§ 371 (c)(1),
(2) Date: Apr. 29, 2020

(87) PCT Pub. No.: WO2019/138400
PCT Pub. Date: Jul. 18, 2019

(65) Prior Publication Data
US 2020/0352760 A1    Nov. 12, 2020

(30) Foreign Application Priority Data

Jan. 10, 2018   (GB) ...................... 1800399

(51) Int. Cl.
*A61F 2/95*     (2013.01)
*B21D 39/04*    (2006.01)
*A61F 2/24*     (2006.01)

(52) U.S. Cl.
CPC .......... *A61F 2/2415* (2013.01); *A61F 2/2427* (2013.01); *A61F 2/9522* (2020.05);
(Continued)

(58) Field of Classification Search
CPC .... A61F 2/2415; A61F 2/9522; A61F 2/9524; B21D 39/048; Y10T 29/49865
See application file for complete search history.

(56) References Cited

U.S. PATENT DOCUMENTS

| 4,222,126 A | 9/1980 | Boretos et al. |
| 4,261,342 A | 4/1981 | Aranguren |

(Continued)

FOREIGN PATENT DOCUMENTS

| CN | 103974674 | 8/2014 |
| CN | 103997990 | 8/2014 |

(Continued)

OTHER PUBLICATIONS

European Search Report dated Jun. 10, 2021 which issued during the prosecution of Applicant's European App No. 21157988.3.
(Continued)

*Primary Examiner* — Jermie E Cozart
(74) *Attorney, Agent, or Firm* — Dilworth IP, LLC

(57) ABSTRACT

An assembly (10) for crimping a frame (56) of an implant (58) comprises a crimping device (20) with a base (22) and a crimping mechanism (24) that defines a crimping aperture (26). A bath (28) having a floor (30), and one or more side-walls (32) extending upward from the floor to a side-wall height defines a receptacle (18) that is shaped to receive a portion of the crimping device. The apparatus has an assembled state in which the portion of the crimping device has been received by the receptacle, the crimping device is held securely by the bath, and the aperture is below the side-wall height. Other embodiments are also described.

26 Claims, 13 Drawing Sheets

(52) U.S. Cl.
CPC .......... *A61F 2/9525* (2020.05); *B21D 39/048* (2013.01); *A61F 2210/0014* (2013.01); *Y10T 29/49865* (2015.01)

(56) References Cited

U.S. PATENT DOCUMENTS

| | | | |
|---|---|---|---|
| 4,275,469 A | 6/1981 | Gabbay | |
| 4,423,525 A | 1/1984 | Vallana et al. | |
| 4,853,986 A | 8/1989 | Allen | |
| 4,892,541 A | 1/1990 | Alonso | |
| 4,972,494 A | 11/1990 | White et al. | |
| 4,994,077 A | 2/1991 | Dobben | |
| 5,078,739 A | 1/1992 | Martin | |
| 5,108,420 A | 4/1992 | Marks | |
| 5,201,757 A | 4/1993 | Heyn et al. | |
| 5,314,473 A | 5/1994 | Godin | |
| 5,332,402 A | 7/1994 | Teitelbaum | |
| 5,397,351 A | 3/1995 | Pavcnik et al. | |
| 5,405,378 A | 4/1995 | Strecker | |
| 5,443,500 A | 8/1995 | Sigwart | |
| 5,473,812 A | 12/1995 | Morris et al. | |
| 5,607,444 A | 3/1997 | Lam | |
| 5,607,470 A | 3/1997 | Milo | |
| 5,647,857 A | 7/1997 | Anderson et al. | |
| 5,702,397 A | 12/1997 | Goble et al. | |
| 5,713,948 A | 2/1998 | Uflacker | |
| 5,765,682 A | 6/1998 | Bley et al. | |
| 5,776,140 A | 7/1998 | Cottone | |
| 5,868,777 A | 2/1999 | Lam | |
| 5,873,906 A | 2/1999 | Lau et al. | |
| 5,954,766 A | 9/1999 | Zadno-Azizi et al. | |
| 5,957,949 A | 9/1999 | Leonhardt et al. | |
| 5,980,565 A | 11/1999 | Jayaraman | |
| 6,010,530 A | 1/2000 | Goicoechea | |
| 6,019,787 A | 2/2000 | Richard et al. | |
| 6,042,607 A | 3/2000 | Williamson, IV | |
| 6,059,827 A | 5/2000 | Fenton | |
| 6,074,417 A | 6/2000 | Peredo | |
| 6,113,612 A | 9/2000 | Swanson et al. | |
| 6,120,534 A | 9/2000 | Ruiz | |
| 6,126,686 A | 10/2000 | Badylak et al. | |
| 6,152,937 A | 11/2000 | Peterson et al. | |
| 6,165,210 A | 12/2000 | Lau et al. | |
| 6,187,020 B1 | 2/2001 | Zegdi et al. | |
| 6,193,686 B1 | 2/2001 | Estrada et al. | |
| 6,193,745 B1 | 2/2001 | Fogarty et al. | |
| 6,254,609 B1 | 7/2001 | Vrba et al. | |
| 6,264,700 B1 | 7/2001 | Kilcoyne et al. | |
| 6,287,339 B1 | 9/2001 | Vasquez et al. | |
| 6,312,465 B1 | 11/2001 | Griffin et al. | |
| 6,332,893 B1 | 12/2001 | Mortier et al. | |
| 6,334,873 B1 | 1/2002 | Lane et al. | |
| 6,350,278 B1 | 2/2002 | Lenker et al. | |
| 6,352,561 B1 | 3/2002 | Leopold et al. | |
| 6,391,036 B1 | 5/2002 | Berg et al. | |
| 6,402,780 B2 | 6/2002 | Williamson, IV | |
| 6,409,755 B1 | 6/2002 | Vrba | |
| 6,419,696 B1 | 7/2002 | Ortiz et al. | |
| 6,428,550 B1 | 8/2002 | Vargas et al. | |
| 6,440,164 B1 | 8/2002 | Dimatteo et al. | |
| 6,454,799 B1 | 9/2002 | Schreck | |
| 6,458,153 B1 | 10/2002 | Bailey et al. | |
| 6,478,807 B1 | 11/2002 | Foreman et al. | |
| 6,482,228 B1 | 11/2002 | Norred | |
| 6,491,711 B1 | 12/2002 | Durcan | |
| 6,511,491 B2 | 1/2003 | Grudem et al. | |
| 6,530,952 B2 | 3/2003 | Vesely | |
| 6,540,782 B1 | 4/2003 | Snyders | |
| 6,551,350 B1 | 4/2003 | Thornton et al. | |
| 6,558,396 B1 | 5/2003 | Inoue | |
| 6,558,418 B2 | 5/2003 | Carpentier et al. | |
| 6,569,196 B1 | 5/2003 | Vesely | |
| 6,602,263 B1 | 8/2003 | Swanson et al. | |
| 6,616,675 B1 | 9/2003 | Evard et al. | |
| 6,652,556 B1 | 11/2003 | VanTessel et al. | |
| 6,669,724 B2 | 12/2003 | Park et al. | |
| 6,682,558 B2 | 1/2004 | Tu et al. | |
| 6,699,256 B1 | 3/2004 | Logan et al. | |
| 6,716,244 B2 | 4/2004 | Klaco | |
| 6,719,781 B1 | 4/2004 | Kim | |
| 6,719,788 B2 | 4/2004 | Cox | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,764,518 B2 | 7/2004 | Godin | |
| 6,767,362 B2 | 7/2004 | Schreck | |
| 6,797,002 B2 | 9/2004 | Spence et al. | |
| 6,821,297 B2 | 11/2004 | Snyders | |
| 6,830,585 B1 | 12/2004 | Artof et al. | |
| 6,830,638 B2 | 12/2004 | Boylan et al. | |
| 6,884,257 B1 | 4/2005 | Cox | |
| 6,893,460 B2 | 5/2005 | Spenser et al. | |
| 6,951,571 B1 | 10/2005 | Srivastava | |
| 6,960,217 B2 | 11/2005 | Bolduc | |
| 6,964,684 B2 | 11/2005 | Ortiz et al. | |
| 6,974,476 B2 | 12/2005 | McGuckin et al. | |
| 7,011,681 B2 | 3/2006 | Vesely | |
| 7,018,406 B2 | 3/2006 | Seguin et al. | |
| 7,041,132 B2 | 5/2006 | Quijano et al. | |
| 7,074,236 B2 | 7/2006 | Rabkin et al. | |
| 7,077,861 B2 | 7/2006 | Spence | |
| 7,101,395 B2 | 9/2006 | Tremulis et al. | |
| 7,101,396 B2 | 9/2006 | Artof et al. | |
| 7,137,184 B2 | 11/2006 | Schreck | |
| 7,172,625 B2 | 2/2007 | Shu et al. | |
| 7,175,656 B2 | 2/2007 | Khairkhahan | |
| 7,198,646 B2 | 4/2007 | Figulla et al. | |
| 7,201,772 B2 | 4/2007 | Schwammenthal | |
| 7,226,477 B2 | 6/2007 | Cox | |
| 7,261,686 B2 | 8/2007 | Couvillon, Jr. | |
| 7,288,111 B1 | 10/2007 | Holloway et al. | |
| 7,316,716 B2 | 1/2008 | Egan | |
| 7,329,279 B2 | 2/2008 | Haug et al. | |
| 7,335,213 B1 | 2/2008 | Hyde et al. | |
| 7,351,256 B2 | 4/2008 | Hojeibane et al. | |
| 7,374,573 B2 | 5/2008 | Gabbay | |
| 7,377,938 B2 | 5/2008 | Sarac et al. | |
| 7,381,218 B2 | 6/2008 | Schreck | |
| 7,381,219 B2 | 6/2008 | Salahieh et al. | |
| 7,404,824 B1 | 7/2008 | Webler et al. | |
| 7,422,603 B2 | 9/2008 | Lane | |
| 7,429,269 B2 | 9/2008 | Schwammenthal | |
| 7,442,204 B2 | 10/2008 | Schwammenthal | |
| 7,445,630 B2 | 11/2008 | Lashinski et al. | |
| 7,455,677 B2 | 11/2008 | Vargas et al. | |
| 7,455,688 B2 | 11/2008 | Furst et al. | |
| 7,462,162 B2 | 12/2008 | Phan et al. | |
| 7,481,838 B2 | 1/2009 | Carpentier et al. | |
| 7,510,575 B2 | 3/2009 | Spenser et al. | |
| 7,513,909 B2 | 4/2009 | Lane et al. | |
| 7,524,331 B2 | 4/2009 | Birdsall | |
| 7,527,646 B2 | 5/2009 | Randert et al. | |
| 7,556,646 B2 | 7/2009 | Yang et al. | |
| 7,582,111 B2 | 9/2009 | Krolik et al. | |
| 7,585,321 B2 | 9/2009 | Cribier | |
| 7,597,711 B2 | 10/2009 | Drews et al. | |
| 7,611,534 B2 | 11/2009 | Kapadia et al. | |
| 7,621,948 B2 | 11/2009 | Hermann et al. | |
| 7,625,403 B2 | 12/2009 | Krivoruchko | |
| 7,632,302 B2 | 12/2009 | Vreeman et al. | |
| 7,648,528 B2 | 1/2010 | Styrc | |
| 7,666,204 B2 | 2/2010 | Thornton et al. | |
| 7,682,380 B2 | 3/2010 | Thornton et al. | |
| 7,708,775 B2 | 5/2010 | Rowe et al. | |
| 7,717,952 B2 | 5/2010 | Case et al. | |
| 7,717,955 B2 | 5/2010 | Lane et al. | |
| 7,731,741 B2 | 6/2010 | Eidenschink | |
| 7,748,389 B2 | 7/2010 | Salahieh et al. | |
| 7,753,922 B2 | 7/2010 | Starksen | |
| 7,753,949 B2 | 7/2010 | Lamphere | |
| 7,758,595 B2 | 7/2010 | Allen et al. | |
| 7,758,632 B2 | 7/2010 | Hojeibane et al. | |
| 7,758,640 B2 | 7/2010 | Vesely | |
| 7,771,467 B2 | 8/2010 | Svensson | |

(56) References Cited

U.S. PATENT DOCUMENTS

| | | |
|---|---|---|
| 7,771,469 B2 | 8/2010 | Liddicoat |
| 7,776,080 B2 | 8/2010 | Bei et al. |
| 7,776,083 B2 | 8/2010 | Vesely |
| 7,780,726 B2 | 8/2010 | Seguin |
| 7,785,341 B2 | 8/2010 | Forster et al. |
| 7,799,069 B2 | 9/2010 | Bailey et al. |
| 7,803,181 B2 | 9/2010 | Furst et al. |
| 7,811,296 B2 | 10/2010 | Goldfarb |
| 7,811,316 B2 | 10/2010 | Kalmann et al. |
| 7,824,442 B2 | 11/2010 | Salahieh et al. |
| 7,837,645 B2 | 11/2010 | Bessler et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,927,370 B2 | 4/2011 | Webler et al. |
| 7,942,927 B2 | 5/2011 | Kaye et al. |
| 7,947,072 B2 | 5/2011 | Yang et al. |
| 7,947,075 B2 | 5/2011 | Goetz et al. |
| 7,951,195 B2 | 5/2011 | Antonsson et al. |
| 7,955,375 B2 | 6/2011 | Agnew |
| 7,955,377 B2 | 6/2011 | Melsheimer |
| 7,955,384 B2 | 6/2011 | Rafiee et al. |
| 7,959,666 B2 | 6/2011 | Salahieh et al. |
| 7,959,672 B2 | 6/2011 | Salahieh et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 | 8/2011 | Hirotsuka et al. |
| 7,993,393 B2 | 8/2011 | Carpentier et al. |
| 8,002,825 B2 | 8/2011 | Letac et al. |
| 8,002,826 B2 | 8/2011 | Seguin |
| 8,016,877 B2 | 9/2011 | Seguin et al. |
| 8,016,882 B2 | 9/2011 | Macoviak et al. |
| 8,021,420 B2 | 9/2011 | Dolan |
| 8,021,421 B2 | 9/2011 | Fogarty et al. |
| 8,025,695 B2 | 9/2011 | Fogarty et al. |
| 8,029,518 B2 | 10/2011 | Goldfarb et al. |
| 8,029,557 B2 | 10/2011 | Sobrino-Serrano et al. |
| 8,029,564 B2 | 10/2011 | Johnson et al. |
| 8,034,104 B2 | 10/2011 | Carpentier et al. |
| 8,038,720 B2 | 10/2011 | Wallace et al. |
| 8,043,360 B2 | 10/2011 | McNamara et al. |
| 8,048,138 B2 | 11/2011 | Sulivan et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,057,493 B2 | 11/2011 | Goldfarb et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,800 B2 | 12/2011 | Lock et al. |
| 8,070,802 B2 | 12/2011 | Lamphere et al. |
| 8,070,804 B2 | 12/2011 | Hyde |
| 8,075,611 B2 | 12/2011 | Milwee et al. |
| 8,080,054 B2 | 12/2011 | Rowe |
| 8,083,793 B2 | 12/2011 | Lane et al. |
| D652,927 S | 1/2012 | Braido et al. |
| D653,341 S | 1/2012 | Braido et al. |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,109,996 B2 | 2/2012 | Stacchino et al. |
| 8,118,866 B2 | 2/2012 | Herrmann et al. |
| 8,133,270 B2 | 3/2012 | Kheradvar et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Randert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,008 B2 | 4/2012 | Wilson et al. |
| 8,163,014 B2 | 4/2012 | Lane et al. |
| D660,433 S | 5/2012 | Braido et al. |
| D660,967 S | 5/2012 | Braido et al. |
| 8,167,894 B2 | 5/2012 | Miles et al. |
| 8,167,932 B2 | 5/2012 | Bourang et al. |
| 8,167,935 B2 | 5/2012 | McGuckin, Jr. et al. |
| 8,172,896 B2 | 5/2012 | McNamara et al. |
| 8,172,898 B2 | 5/2012 | Alferness et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,216,301 B2 | 7/2012 | Bonhoeffer et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,267,988 B2 | 9/2012 | Hamer et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,303,653 B2 | 11/2012 | Bonhoeffer et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,337,541 B2 | 12/2012 | Quadri et al. |
| 8,343,174 B2 | 1/2013 | Goldfarb et al. |
| 8,343,213 B2 | 1/2013 | Salahieh et al. |
| 8,348,999 B2 | 1/2013 | Kheradvar et al. |
| 8,361,144 B2 | 1/2013 | Fish et al. |
| 8,366,767 B2 | 2/2013 | Zhang |
| 8,372,140 B2 | 2/2013 | Hoffman et al. |
| 8,377,119 B2 | 2/2013 | Drews et al. |
| 8,398,708 B2 | 3/2013 | Meiri et al. |
| 8,403,981 B2 | 3/2013 | Forster et al. |
| 8,403,983 B2 | 3/2013 | Quadri et al. |
| 8,408,214 B2 | 4/2013 | Spenser |
| 8,414,644 B2 | 4/2013 | Quadri et al. |
| 8,425,593 B2 | 4/2013 | Braido et al. |
| 8,430,934 B2 | 4/2013 | Das |
| 8,444,689 B2 | 5/2013 | Zhang |
| 8,449,599 B2 | 5/2013 | Chau et al. |
| 8,449,625 B2 | 5/2013 | Campbell et al. |
| 8,454,686 B2 | 6/2013 | Alkhatib |
| 8,460,365 B2 | 6/2013 | Haverkost et al. |
| 8,474,460 B2 | 7/2013 | Barrett et al. |
| 8,500,821 B2 | 8/2013 | Sobrino-Serrano et al. |
| 8,512,400 B2 | 8/2013 | Tran et al. |
| 8,539,662 B2 | 9/2013 | Stacchino et al. |
| 8,540,767 B2 | 9/2013 | Zhang |
| 8,545,544 B2 | 10/2013 | Spenser et al. |
| 8,551,160 B2 | 10/2013 | Figulla et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,460 B2 | 11/2013 | Wilson et al. |

(56) References Cited

U.S. PATENT DOCUMENTS

| | | |
|---|---|---|
| 8,591,570 B2 | 11/2013 | Revuelta et al. |
| 8,623,075 B2 | 1/2014 | Murray et al. |
| 8,623,080 B2 | 1/2014 | Fogarty et al. |
| 8,628,569 B2 | 1/2014 | Benichou et al. |
| 8,628,570 B2 | 1/2014 | Seguin |
| 8,628,571 B1 | 1/2014 | Hacohen et al. |
| 8,652,203 B2 | 2/2014 | Quadri et al. |
| 8,652,204 B2 | 2/2014 | Quill et al. |
| 8,657,872 B2 | 2/2014 | Seguin |
| 8,663,322 B2 | 3/2014 | Keranen |
| 8,673,020 B2 | 3/2014 | Sobrino-Serrano et al. |
| 8,679,174 B2 | 3/2014 | Ottma et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,734,507 B2 | 5/2014 | Keranen |
| 8,747,460 B2 | 6/2014 | Tuval et al. |
| 8,771,345 B2 | 7/2014 | Tuval et al. |
| 8,784,472 B2 | 7/2014 | Eidenschink |
| 8,784,479 B2 | 7/2014 | Antonsson et al. |
| 8,784,481 B2 | 7/2014 | Alkhatib et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,801,776 B2 | 8/2014 | House et al. |
| 8,808,366 B2 | 8/2014 | Braido et al. |
| 8,840,663 B2 | 9/2014 | Salahieh et al. |
| 8,840,664 B2 | 9/2014 | Karapetian et al. |
| 8,845,722 B2 | 9/2014 | Gabbay |
| 8,852,261 B2 | 10/2014 | White |
| 8,852,272 B2 | 10/2014 | Gross et al. |
| 8,870,948 B1 | 10/2014 | Erzberger et al. |
| 8,870,949 B2 | 10/2014 | Rowe |
| 8,870,950 B2 | 10/2014 | Hacohen |
| 8,876,800 B2 | 11/2014 | Behan |
| 8,894,702 B2 | 11/2014 | Quadri et al. |
| 8,900,294 B2 | 12/2014 | Paniagua et al. |
| 8,900,295 B2 | 12/2014 | Migliazza et al. |
| 8,906,083 B2 | 12/2014 | Obermiller et al. |
| 8,911,455 B2 | 12/2014 | Quadri et al. |
| 8,911,489 B2 | 12/2014 | Ben-Muvhar |
| 8,911,493 B2 | 12/2014 | Rowe et al. |
| 8,932,343 B2 | 1/2015 | Alkhatib et al. |
| 8,945,177 B2 | 2/2015 | Dell |
| 8,961,595 B2 | 2/2015 | Alkhatib |
| 8,979,922 B2 | 3/2015 | Jayasinghe et al. |
| 8,986,370 B2 | 3/2015 | Annest |
| 8,986,373 B2 | 3/2015 | Chau et al. |
| 8,986,375 B2 | 3/2015 | Garde et al. |
| 8,992,599 B2 | 3/2015 | Thubrikar et al. |
| 8,992,604 B2 | 3/2015 | Gross et al. |
| 8,992,608 B2 | 3/2015 | Haug et al. |
| 8,998,982 B2 | 4/2015 | Richter et al. |
| 9,005,273 B2 | 4/2015 | Salahieh et al. |
| 9,011,468 B2 | 4/2015 | Ketai |
| 9,011,527 B2 | 4/2015 | Li et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| D732,666 S | 6/2015 | Nguyen et al. |
| 9,050,188 B2 | 6/2015 | Schweich et al. |
| 9,072,603 B2 | 7/2015 | Tuval et al. |
| 9,084,676 B2 | 7/2015 | Chau et al. |
| 9,095,434 B2 | 8/2015 | Rowe |
| 9,119,719 B2 | 9/2015 | Zipory |
| 9,125,738 B2 | 9/2015 | Figulla et al. |
| 9,125,740 B2 | 9/2015 | Morriss et al. |
| 9,132,006 B2 | 9/2015 | Spenser et al. |
| 9,132,009 B2 | 9/2015 | Hacohen et al. |
| 9,138,312 B2 | 9/2015 | Tuval et al. |
| 9,155,619 B2 | 10/2015 | Liu et al. |
| 9,173,659 B2 | 11/2015 | Bodewadt et al. |
| 9,173,738 B2 | 11/2015 | Murray et al. |
| 9,220,594 B2 | 12/2015 | Braido et al. |
| 9,226,820 B2 | 1/2016 | Braido et al. |
| 9,226,839 B1 | 1/2016 | Kariniemi et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,241,794 B2 | 1/2016 | Braido et al. |
| 9,248,014 B2 | 2/2016 | Lane et al. |
| 9,277,994 B2 | 3/2016 | Miller |
| 9,289,290 B2 | 3/2016 | Alkhatib et al. |
| 9,289,291 B2 | 3/2016 | Gorman et al. |
| 9,295,550 B2 | 3/2016 | Nguyen et al. |
| 9,295,551 B2 | 3/2016 | Straubinger et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,320,591 B2 | 4/2016 | Bolduc |
| D755,384 S | 5/2016 | Pesce et al. |
| 9,326,852 B2 | 5/2016 | Spenser |
| 9,326,876 B2 | 5/2016 | Acosta et al. |
| 9,345,573 B2 | 5/2016 | Nyuli et al. |
| 9,387,078 B2 | 7/2016 | Gross et al. |
| 9,393,110 B2 | 7/2016 | Levi et al. |
| 9,421,098 B2 | 8/2016 | Gifford et al. |
| 9,427,303 B2 | 8/2016 | Liddy et al. |
| 9,427,316 B2 | 8/2016 | Schweich, Jr. et al. |
| 9,439,757 B2 | 9/2016 | Wallace et al. |
| 9,463,102 B2 | 10/2016 | Kelly |
| 9,474,599 B2 | 10/2016 | Keränen |
| 9,474,638 B2 | 10/2016 | Robinson et al. |
| 9,480,559 B2 | 11/2016 | Vidlund et al. |
| 9,492,273 B2 | 11/2016 | Wallace et al. |
| 9,498,314 B2 | 11/2016 | Behan |
| 9,498,332 B2 | 11/2016 | Hacohen et al. |
| 9,510,947 B2 | 12/2016 | Straubinger et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,743,932 B2 | 8/2017 | Amplatz et al. |
| 9,763,657 B2 | 9/2017 | Hacohen et al. |
| 9,763,817 B2 | 9/2017 | Roeder |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 9,987,132 B1 | 6/2018 | Hariton et al. |
| 10,010,414 B2 | 7/2018 | Cooper et al. |
| 10,045,845 B2 | 8/2018 | Hacohen et al. |
| 10,098,732 B1 | 10/2018 | Hariton et al. |
| 10,105,222 B1 | 10/2018 | Metchik |
| 10,123,873 B1 | 11/2018 | Metchik |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,292,816 B2 | 5/2019 | Raanani |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,376,361 B2 | 8/2019 | Gross et al. |
| 10,390,952 B2 | 8/2019 | Hariton |
| 10,426,614 B2 | 10/2019 | Hariton et al. |
| 10,449,047 B2 | 10/2019 | Hariton et al. |

(56) References Cited

U.S. PATENT DOCUMENTS

| | | |
|---|---|---|
| 10,492,908 B2 | 12/2019 | Hammer et al. |
| 10,507,108 B2 | 12/2019 | Delgado |
| 10,512,456 B2 | 12/2019 | Hacohen |
| 10,517,719 B2 | 12/2019 | Miller |
| 10,524,910 B2 | 1/2020 | Hammer et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,610,358 B2 | 4/2020 | Vidlund |
| 10,631,871 B2 | 4/2020 | Goldfarb |
| 10,667,908 B2 | 6/2020 | Hariton et al. |
| 10,667,912 B2 | 6/2020 | Dixon |
| 10,682,227 B2 | 6/2020 | Hariton et al. |
| 10,695,177 B2 | 6/2020 | Hariton et al. |
| 10,702,385 B2 | 7/2020 | Hacohen |
| 10,736,742 B2 | 8/2020 | Hariton et al. |
| 10,758,342 B2 | 9/2020 | Chau et al. |
| 10,842,627 B2 | 11/2020 | Delgado |
| 10,856,972 B2 | 12/2020 | Hariton |
| 10,856,975 B2 | 12/2020 | Hariton et al. |
| 10,856,978 B2 | 12/2020 | Straubinger et al. |
| 10,874,514 B2 | 12/2020 | Dixon |
| 10,888,422 B2 | 1/2021 | Hariton |
| 10,888,425 B2 | 1/2021 | Delgado |
| 10,888,644 B2 | 1/2021 | Ratz |
| 10,905,552 B2 | 2/2021 | Dixon |
| 10,905,554 B2 | 2/2021 | Cao |
| 10,918,483 B2 | 2/2021 | Metchik |
| 10,925,732 B2 | 2/2021 | Delgado |
| 10,945,843 B2 | 3/2021 | Delgado |
| 10,945,844 B2 | 3/2021 | McCann |
| 10,959,846 B2 | 3/2021 | Marr |
| 10,993,809 B2 | 5/2021 | McCann |
| 11,065,114 B2 | 7/2021 | Raanani |
| 11,083,582 B2 | 8/2021 | McCann |
| 11,147,672 B2 | 10/2021 | McCann |
| 11,179,240 B2 | 11/2021 | Delgado |
| 11,291,545 B2 | 4/2022 | Hacohen |
| 11,291,546 B2 | 4/2022 | Gross |
| 11,291,547 B2 | 4/2022 | Gross |
| 11,304,806 B2 | 4/2022 | Hariton |
| 11,389,297 B2 | 7/2022 | Franklin |
| 2001/0002445 A1 | 5/2001 | Vesely |
| 2001/0005787 A1 | 6/2001 | Oz |
| 2001/0021872 A1 | 9/2001 | Bailey et al. |
| 2001/0056295 A1 | 12/2001 | Solem |
| 2002/0032481 A1 | 3/2002 | Gabbay |
| 2002/0099436 A1 | 7/2002 | Thornton et al. |
| 2002/0151970 A1 | 10/2002 | Garrison et al. |
| 2002/0177894 A1 | 11/2002 | Acosta et al. |
| 2003/0009236 A1 | 1/2003 | Godin |
| 2003/0036791 A1 | 2/2003 | Bonhoeffer et al. |
| 2003/0050694 A1 | 3/2003 | Yang et al. |
| 2003/0060875 A1 | 3/2003 | Wittens |
| 2003/0069635 A1 | 4/2003 | Cartledge |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0010272 A1 | 1/2004 | Manetakis et al. |
| 2004/0039414 A1 | 2/2004 | Carley et al. |
| 2004/0093060 A1 | 5/2004 | Seguin et al. |
| 2004/0122503 A1 | 6/2004 | Campbell et al. |
| 2004/0122514 A1 | 6/2004 | Fogarty et al. |
| 2004/0133267 A1 | 7/2004 | Lane |
| 2004/0143315 A1 | 7/2004 | Bruun et al. |
| 2004/0176839 A1 | 9/2004 | Huynh et al. |
| 2004/0186558 A1 | 9/2004 | Pavcnik et al. |
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0210304 A1 | 10/2004 | Seguin et al. |
| 2004/0220593 A1 | 11/2004 | Greenhalgh |
| 2004/0225354 A1 | 11/2004 | Allen et al. |
| 2004/0249433 A1 | 12/2004 | Freitag |
| 2004/0260389 A1 | 12/2004 | Case et al. |
| 2004/0260394 A1 | 12/2004 | Douk et al. |
| 2005/0004668 A1 | 1/2005 | Aklog et al. |
| 2005/0021056 A1 | 1/2005 | St. Goar et al. |
| 2005/0027305 A1 | 2/2005 | Shiu et al. |
| 2005/0027348 A1 | 2/2005 | Case et al. |
| 2005/0038494 A1 | 2/2005 | Eidenschink |
| 2005/0055086 A1 | 3/2005 | Stobie |
| 2005/0075731 A1 | 4/2005 | Artof et al. |
| 2005/0080430 A1 | 4/2005 | Wright et al. |
| 2005/0080474 A1 | 4/2005 | Andreas et al. |
| 2005/0085900 A1 | 4/2005 | Case et al. |
| 2005/0137686 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh |
| 2005/0137692 A1 | 6/2005 | Haug et al. |
| 2005/0137693 A1 | 6/2005 | Haug |
| 2005/0137695 A1 | 6/2005 | Salahieh et al. |
| 2005/0137697 A1 | 6/2005 | Salahieh et al. |
| 2005/0137699 A1 | 6/2005 | Salahieh |
| 2005/0143809 A1 | 6/2005 | Salahieh et al. |
| 2005/0149160 A1 | 7/2005 | McFerran |
| 2005/0154443 A1 | 7/2005 | Linder et al. |
| 2005/0182483 A1 | 8/2005 | Osborne et al. |
| 2005/0182486 A1 | 8/2005 | Gabbay |
| 2005/0197695 A1 | 9/2005 | Stacchino et al. |
| 2005/0203549 A1 | 9/2005 | Realyvasquez |
| 2005/0203618 A1 | 9/2005 | Sharkawy et al. |
| 2005/0216079 A1 | 9/2005 | MaCoviak |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0256566 A1 | 11/2005 | Gabbay |
| 2005/0267573 A9 | 12/2005 | Macoviak et al. |
| 2006/0004439 A1 | 1/2006 | Spenser et al. |
| 2006/0004469 A1 | 1/2006 | Sokel |
| 2006/0015171 A1 | 1/2006 | Armstrong |
| 2006/0020275 A1 | 1/2006 | Goldfarb |
| 2006/0020327 A1 | 1/2006 | Lashinski et al. |
| 2006/0020333 A1 | 1/2006 | Lashinski et al. |
| 2006/0041189 A1 | 2/2006 | Vancaillie |
| 2006/0052867 A1 | 3/2006 | Revuelta et al. |
| 2006/0089627 A1 | 4/2006 | Burnett et al. |
| 2006/0111773 A1 | 5/2006 | Rittgers et al. |
| 2006/0116750 A1 | 6/2006 | Herbert et al. |
| 2006/0135964 A1 | 6/2006 | Vesley |
| 2006/0155357 A1 | 7/2006 | Melsheimer |
| 2006/0161250 A1 | 7/2006 | Shaw |
| 2006/0047297 A1 | 8/2006 | Case |
| 2006/0178700 A1 | 8/2006 | Quinn |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195183 A1 | 8/2006 | Navia et al. |
| 2006/0195184 A1 | 8/2006 | Lane et al. |
| 2006/0201519 A1 | 9/2006 | Frazier et al. |
| 2006/0212111 A1 | 9/2006 | Case et al. |
| 2006/0216404 A1 | 9/2006 | Seyler et al. |
| 2006/0241656 A1 | 10/2006 | Starksen et al. |
| 2006/0241745 A1 | 10/2006 | Solem |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0259137 A1 | 11/2006 | Artof et al. |
| 2006/0271166 A1 | 11/2006 | Thill et al. |
| 2006/0271171 A1 | 11/2006 | McQuinn et al. |
| 2006/0282150 A1 | 12/2006 | Olson et al. |
| 2006/0287719 A1 | 12/2006 | Rowe et al. |
| 2007/0016286 A1 | 1/2007 | Herrmann |
| 2007/0016288 A1 | 1/2007 | Gurskis et al. |
| 2007/0027528 A1 | 2/2007 | Agnew |
| 2007/0027549 A1 | 2/2007 | Godin |
| 2007/0038295 A1 | 2/2007 | Case et al. |
| 2007/0043435 A1 | 2/2007 | Seguin et al. |

(56) References Cited

U.S. PATENT DOCUMENTS

| | | |
|---|---|---|
| 2007/0055340 A1 | 3/2007 | Pryor |
| 2007/0056346 A1 | 3/2007 | Spenser et al. |
| 2007/0078510 A1 | 4/2007 | Ryan |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0197858 A1 | 8/2007 | Goldfarb |
| 2007/0198077 A1 | 8/2007 | Cully et al. |
| 2007/0198097 A1 | 8/2007 | Zegdi |
| 2007/0213810 A1 | 9/2007 | Newhauser et al. |
| 2007/0213813 A1 | 9/2007 | Von Segesser et al. |
| 2007/0219630 A1 | 9/2007 | Chu |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0239273 A1 | 10/2007 | Allen |
| 2007/0244546 A1 | 10/2007 | Francis |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0051703 A1 | 2/2008 | Thornton et al. |
| 2008/0065204 A1 | 3/2008 | Macoviak |
| 2008/0071361 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0082083 A1 | 4/2008 | Forde et al. |
| 2008/0082159 A1 | 4/2008 | Tseng et al. |
| 2008/0082166 A1 | 4/2008 | Styrc et al. |
| 2008/0086164 A1 | 4/2008 | Rowe et al. |
| 2008/0086204 A1 | 4/2008 | Rankin |
| 2008/0091261 A1 | 4/2008 | Long et al. |
| 2008/0097595 A1 | 4/2008 | Gabbay |
| 2008/0132989 A1 | 6/2008 | Snow et al. |
| 2008/0140003 A1 | 6/2008 | Bei et al. |
| 2008/0147182 A1 | 6/2008 | Righini et al. |
| 2008/0161910 A1 | 7/2008 | Revuelta et al. |
| 2008/0167705 A1 | 7/2008 | Agnew |
| 2008/0167714 A1 | 7/2008 | St. Goar et al. |
| 2008/0188929 A1 | 8/2008 | Schreck |
| 2008/0195200 A1 | 8/2008 | Vidlund et al. |
| 2008/0200980 A1 | 8/2008 | Robin et al. |
| 2008/0208328 A1 | 8/2008 | Antocci |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0243245 A1 | 10/2008 | Thambar et al. |
| 2008/0255580 A1 | 10/2008 | Hoffman et al. |
| 2008/0262609 A1 | 10/2008 | Gross et al. |
| 2008/0269879 A1 | 10/2008 | Sathe et al. |
| 2008/0281411 A1 | 11/2008 | Berreklouw |
| 2008/0294234 A1 | 11/2008 | Hartley et al. |
| 2009/0005863 A1 | 1/2009 | Goetz et al. |
| 2009/0036966 A1 | 2/2009 | O'Connor et al. |
| 2009/0054969 A1 | 2/2009 | Salahieh et al. |
| 2009/0082844 A1 | 3/2009 | Zacharias |
| 2009/0088836 A1 | 4/2009 | Bishop et al. |
| 2009/0099554 A1 | 4/2009 | Forster et al. |
| 2009/0099650 A1 | 4/2009 | Bolduc et al. |
| 2009/0112159 A1 | 4/2009 | Slattery et al. |
| 2009/0125098 A1 | 5/2009 | Chuter |
| 2009/0157175 A1 | 6/2009 | Benichou |
| 2009/0163934 A1 | 6/2009 | Raschdorf, Jr. |
| 2009/0171363 A1 | 7/2009 | Chocron |
| 2009/0177278 A1 | 7/2009 | Spence |
| 2009/0210052 A1 | 8/2009 | Forster et al. |
| 2009/0222081 A1 | 9/2009 | Linder et al. |
| 2009/0240320 A1 | 9/2009 | Tuval et al. |
| 2009/0241656 A1 | 10/2009 | Jacquemin |
| 2009/0248143 A1 | 10/2009 | Laham |
| 2009/0259306 A1 | 10/2009 | Rowe |
| 2009/0264859 A1 | 10/2009 | Mas |
| 2009/0264994 A1 | 10/2009 | Saadat |
| 2009/0276040 A1 | 11/2009 | Rowe et al. |
| 2009/0281619 A1 | 11/2009 | Le et al. |
| 2009/0287304 A1 | 11/2009 | Dahlgren et al. |
| 2009/0299449 A1 | 12/2009 | Styrc |
| 2009/0306768 A1 | 12/2009 | Quardi |
| 2009/0319037 A1 | 12/2009 | Rowe et al. |
| 2010/0022823 A1 | 1/2010 | Goldfarb |
| 2010/0023117 A1 | 1/2010 | Yoganathan et al. |
| 2010/0023120 A1 | 1/2010 | Holecek et al. |
| 2010/0036479 A1 | 2/2010 | Hill et al. |
| 2010/0049313 A1 | 2/2010 | Alon et al. |
| 2010/0069852 A1 | 3/2010 | Kelley |
| 2010/0076548 A1 | 3/2010 | Konno |
| 2010/0100167 A1 | 4/2010 | Bortlein et al. |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0185277 A1 | 7/2010 | Braido |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0256737 A1 | 10/2010 | Pollock et al. |
| 2010/0262232 A1 | 10/2010 | Annest |
| 2010/0280603 A1 | 11/2010 | Maisano et al. |
| 2010/0280606 A1 | 11/2010 | Naor |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004296 A1 | 1/2011 | Lutter et al. |
| 2011/0004299 A1 | 1/2011 | Navia et al. |
| 2011/0015729 A1 | 1/2011 | Jimenez et al. |
| 2011/0015731 A1 | 1/2011 | Carpentier et al. |
| 2011/0015739 A1 | 1/2011 | Cheung et al. |
| 2011/0021985 A1 | 1/2011 | Spargias |
| 2011/0022165 A1 | 1/2011 | Oba et al. |
| 2011/0178597 A9 | 1/2011 | Navia et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0071626 A1 | 3/2011 | Wright et al. |
| 2011/0077730 A1 | 3/2011 | Fentster |
| 2011/0082538 A1 | 4/2011 | Dahlgren et al. |
| 2011/0087322 A1 | 4/2011 | Letac et al. |
| 2011/0093063 A1 | 4/2011 | Schreck |
| 2011/0098525 A1 | 4/2011 | Kermode et al. |
| 2011/0106247 A1 | 5/2011 | Miller et al. |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0144742 A1 | 6/2011 | Madrid et al. |
| 2011/0166636 A1 | 7/2011 | Rowe |
| 2011/0172784 A1 | 7/2011 | Richter et al. |
| 2011/0184510 A1 | 7/2011 | Maisano et al. |
| 2011/0190877 A1 | 8/2011 | Lane et al. |
| 2011/0190879 A1 | 8/2011 | Bobo et al. |

(56) References Cited

U.S. PATENT DOCUMENTS

| | | |
|---|---|---|
| 2011/0202076 A1 | 8/2011 | Richter |
| 2011/0208283 A1 | 8/2011 | Rust |
| 2011/0208293 A1 | 8/2011 | Tabor |
| 2011/0208298 A1 | 8/2011 | Tuval et al. |
| 2011/0213459 A1 | 9/2011 | Garrison et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0238159 A1 | 9/2011 | Guyenot et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251678 A1 | 10/2011 | Eidenschink et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0282439 A1 | 11/2011 | Thill et al. |
| 2011/0282440 A1 | 11/2011 | Cao |
| 2011/0283514 A1 | 11/2011 | Fogarty et al. |
| 2011/0288632 A1 | 11/2011 | White |
| 2011/0288634 A1 | 11/2011 | Tuval et al. |
| 2011/0295354 A1 | 12/2011 | Bueche et al. |
| 2011/0295363 A1 | 12/2011 | Girard et al. |
| 2011/0301688 A1 | 12/2011 | Dolan |
| 2011/0301698 A1 | 12/2011 | Miller et al. |
| 2011/0301701 A1 | 12/2011 | Padala et al. |
| 2011/0301702 A1 | 12/2011 | Rust et al. |
| 2011/0306916 A1 | 12/2011 | Nitzan et al. |
| 2011/0307049 A1 | 12/2011 | Kao |
| 2011/0313452 A1 | 12/2011 | Carley et al. |
| 2011/0313515 A1 | 12/2011 | Quadri et al. |
| 2011/0319989 A1 | 12/2011 | Lane et al. |
| 2011/0319991 A1 | 12/2011 | Hariton et al. |
| 2012/0010694 A1 | 1/2012 | Lutter et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022637 A1 | 1/2012 | Ben-Movhar et al. |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053676 A1 | 3/2012 | Ku et al. |
| 2012/0053682 A1 | 3/2012 | Kovalsky et al. |
| 2012/0053688 A1 | 3/2012 | Fogarty et al. |
| 2012/0059337 A1 | 3/2012 | Eilat |
| 2012/0059454 A1 | 3/2012 | Millwee et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123511 A1 | 5/2012 | Brown |
| 2012/0123529 A1 | 5/2012 | Levi |
| 2012/0123530 A1 | 5/2012 | Carpentier et al. |
| 2012/0130473 A1 | 5/2012 | Norris et al. |
| 2012/0130474 A1 | 5/2012 | Buckley |
| 2012/0130475 A1 | 5/2012 | Shaw |
| 2012/0136434 A1 | 5/2012 | Carpentier et al. |
| 2012/0150218 A1 | 6/2012 | Sandgren et al. |
| 2012/0165915 A1 | 6/2012 | Melsheimer et al. |
| 2012/0165930 A1 | 6/2012 | Gifford, III |
| 2012/0179244 A1 | 7/2012 | Schankereli et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0296360 A1 | 11/2012 | Norris et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0018458 A1 | 1/2013 | Yohanan et al. |
| 2013/0030519 A1 | 1/2013 | Tran |
| 2013/0035759 A1 | 2/2013 | Gross et al. |
| 2013/0041204 A1 | 2/2013 | Heilman et al. |
| 2013/0041451 A1 | 2/2013 | Patterson et al. |
| 2013/0046373 A1 | 2/2013 | Cartledge et al. |
| 2013/0066341 A1 | 3/2013 | Ketai |
| 2013/0066342 A1 | 3/2013 | Dell |
| 2013/0079872 A1 | 3/2013 | Gallagher |
| 2013/0116780 A1 | 5/2013 | Miller et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0172992 A1 | 7/2013 | Gross et al. |
| 2013/0178930 A1 | 7/2013 | Straubinger et al. |
| 2013/0190861 A1 | 7/2013 | Chau et al. |
| 2013/0211501 A1 | 8/2013 | Buckley et al. |
| 2013/0231735 A1 | 9/2013 | Deem et al. |
| 2013/0245742 A1 | 9/2013 | Norris |
| 2013/0253643 A1 | 9/2013 | Rolando |
| 2013/0261737 A1 | 10/2013 | Costello |
| 2013/0261738 A1 | 10/2013 | Clague et al. |
| 2013/0274870 A1 | 10/2013 | Lombardi et al. |
| 2013/0289711 A1 | 10/2013 | Liddy et al. |
| 2013/0289740 A1 | 10/2013 | Liddy et al. |
| 2013/0297013 A1 | 11/2013 | Klima et al. |
| 2013/0304197 A1 | 11/2013 | Buchbinder et al. |
| 2013/0304200 A1 | 11/2013 | McLean et al. |
| 2013/0310928 A1 | 11/2013 | Morriss et al. |
| 2013/0325114 A1 | 12/2013 | McLean et al. |
| 2013/0331929 A1 | 12/2013 | Mitra et al. |
| 2014/0000112 A1 | 1/2014 | Braido et al. |
| 2014/0005778 A1 | 1/2014 | Buchbinder et al. |
| 2014/0018911 A1 | 1/2014 | Zhou et al. |
| 2014/0018915 A1 | 1/2014 | Biadillah et al. |
| 2014/0031928 A1 | 1/2014 | Murphy et al. |
| 2014/0046430 A1 | 2/2014 | Shaw |
| 2014/0052237 A1 | 2/2014 | Lane et al. |
| 2014/0067050 A1 | 3/2014 | Costello et al. |
| 2014/0067054 A1 | 3/2014 | Chau et al. |
| 2014/0081376 A1 | 3/2014 | Burkart et al. |
| 2014/0106951 A1 | 4/2014 | Brandon |
| 2014/0120287 A1 | 5/2014 | Jacoby et al. |

(56) References Cited

U.S. PATENT DOCUMENTS

| | | |
|---|---|---|
| 2014/0121749 A1 | 5/2014 | Roeder |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0142688 A1 | 5/2014 | Duffy et al. |
| 2014/0148891 A1 | 5/2014 | Johnson |
| 2014/0163690 A1 | 6/2014 | White |
| 2014/0172069 A1 | 6/2014 | Roeder et al. |
| 2014/0172077 A1 | 6/2014 | Bruchman et al. |
| 2014/0172082 A1 | 6/2014 | Bruchman et al. |
| 2014/0188210 A1 | 7/2014 | Beard et al. |
| 2014/0188221 A1 | 7/2014 | Chung et al. |
| 2014/0194981 A1 | 7/2014 | Menk et al. |
| 2014/0194983 A1 | 7/2014 | Kovalsky et al. |
| 2014/0207231 A1 | 7/2014 | Hacohen et al. |
| 2014/0214157 A1 | 7/2014 | Georg |
| 2014/0214159 A1 | 7/2014 | Vidlund et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257461 A1 | 9/2014 | Robinson et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277358 A1 | 9/2014 | Slazas |
| 2014/0277409 A1 | 9/2014 | Börtlein et al. |
| 2014/0277411 A1 | 9/2014 | Börtlein et al. |
| 2014/0277412 A1 | 9/2014 | Börtlein |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296962 A1 | 10/2014 | Cartledge et al. |
| 2014/0296969 A1 | 10/2014 | Tegels et al. |
| 2014/0324164 A1 | 10/2014 | Gross et al. |
| 2014/0331475 A1 | 11/2014 | Duffy |
| 2014/0336744 A1 | 11/2014 | Tani et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0018944 A1 | 1/2015 | O'Connor et al. |
| 2015/0032205 A1 | 1/2015 | Matheny |
| 2015/0045880 A1 | 2/2015 | Hacohen |
| 2015/0045881 A1 | 2/2015 | Lim |
| 2015/0094802 A1 | 4/2015 | Buchbinder et al. |
| 2015/0119970 A1 | 4/2015 | Nakayama et al. |
| 2015/0127097 A1 | 5/2015 | Neumann et al. |
| 2015/0142100 A1 | 5/2015 | Morriss et al. |
| 2015/0142103 A1 | 5/2015 | Vidlund |
| 2015/0148894 A1 | 5/2015 | Damm et al. |
| 2015/0157457 A1 | 6/2015 | Hacohen |
| 2015/0157458 A1 | 6/2015 | Thambar et al. |
| 2015/0164640 A1 | 6/2015 | Mclean et al. |
| 2015/0173896 A1 | 6/2015 | Richter et al. |
| 2015/0173897 A1 | 6/2015 | Raanani et al. |
| 2015/0196390 A1 | 7/2015 | Ma |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272731 A1 | 10/2015 | Racchini |
| 2015/0272734 A1 | 10/2015 | Sheps et al. |
| 2015/0282964 A1 | 10/2015 | Beard et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0095700 A1 | 4/2016 | Righini |
| 2016/0100939 A1 | 4/2016 | Armstrong et al. |
| 2016/0106539 A1 | 4/2016 | Buchbinder et al. |
| 2016/0113766 A1 | 4/2016 | Ganesan et al. |
| 2016/0113768 A1 | 4/2016 | Ganesan et al. |
| 2016/0125160 A1 | 5/2016 | Heneghan et al. |
| 2016/0175095 A1 | 6/2016 | Dienno et al. |
| 2016/0213473 A1 | 7/2016 | Hacohen et al. |
| 2016/0220367 A1 | 8/2016 | Barrett |
| 2016/0228247 A1 | 8/2016 | Maimon et al. |
| 2016/0242902 A1 | 8/2016 | Morriss et al. |
| 2016/0270911 A1 | 9/2016 | Ganesan et al. |
| 2016/0296330 A1 | 10/2016 | Hacohen |
| 2016/0310268 A1 | 10/2016 | Oba et al. |
| 2016/0310274 A1 | 10/2016 | Gross et al. |
| 2016/0317301 A1 | 11/2016 | Quadri et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0324640 A1 | 11/2016 | Gifford et al. |
| 2016/0331526 A1 | 11/2016 | Schweich et al. |
| 2016/0331527 A1 | 11/2016 | Vidlund et al. |
| 2016/0338706 A1 | 11/2016 | Rowe |
| 2016/0367360 A1 | 12/2016 | Cartledge et al. |
| 2016/0367368 A1 | 12/2016 | Vidlund et al. |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer |
| 2017/0056166 A1 | 3/2017 | Ratz et al. |
| 2017/0056171 A1 | 3/2017 | Cooper et al. |
| 2017/0065407 A1 | 3/2017 | Hacohen et al. |
| 2017/0065411 A1 | 3/2017 | Grundeman et al. |
| 2017/0100236 A1 | 4/2017 | Robertson |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0196688 A1 | 7/2017 | Christianson et al. |
| 2017/0196692 A1 | 7/2017 | Kirk et al. |
| 2017/0209264 A1 | 7/2017 | Chau et al. |
| 2017/0216026 A1 | 8/2017 | Quill et al. |
| 2017/0224323 A1 | 8/2017 | Rowe et al. |
| 2017/0231757 A1 | 8/2017 | Gassler |
| 2017/0231759 A1 | 8/2017 | Geist et al. |
| 2017/0231760 A1 | 8/2017 | Lane et al. |
| 2017/0231766 A1 | 8/2017 | Hariton et al. |
| 2017/0252159 A1 | 9/2017 | Hacohen et al. |
| 2017/0266003 A1 | 9/2017 | Hammer et al. |
| 2017/0333183 A1 | 11/2017 | Backus |
| 2017/0333187 A1 | 11/2017 | Hariton et al. |
| 2017/0360426 A1 | 12/2017 | Hacohen et al. |
| 2017/0367823 A1 | 12/2017 | Hariton et al. |
| 2018/0000580 A1 | 1/2018 | Wallace et al. |
| 2018/0014930 A1 | 1/2018 | Hariton et al. |
| 2018/0014932 A1 | 1/2018 | Hammer et al. |
| 2018/0021129 A1 | 1/2018 | Peterson et al. |
| 2018/0028311 A1 | 2/2018 | Hacohen |
| 2018/0049873 A1 | 2/2018 | Manash et al. |
| 2018/0055628 A1 | 3/2018 | Patel et al. |
| 2018/0055630 A1 | 3/2018 | Patel et al. |
| 2018/0098850 A1 | 4/2018 | Rafiee |
| 2018/0116790 A1 | 5/2018 | Ratz |
| 2018/0116843 A1 | 5/2018 | Schreck et al. |
| 2018/0125644 A1 | 5/2018 | Conklin |
| 2018/0132999 A1 | 5/2018 | Perouse |
| 2018/0147059 A1 | 5/2018 | Hammer et al. |
| 2018/0153687 A1 | 6/2018 | Hariton et al. |
| 2018/0153689 A1 | 6/2018 | Maimon et al. |
| 2018/0153696 A1 | 6/2018 | Albitov et al. |
| 2018/0161159 A1 | 6/2018 | Lee |
| 2018/0177593 A1 | 6/2018 | Hariton et al. |
| 2018/0177594 A1 | 6/2018 | Patel et al. |

(56) References Cited

U.S. PATENT DOCUMENTS

| | | |
|---|---|---|
| 2018/0185148 A1 | 7/2018 | Hariton et al. |
| 2018/0206983 A1 | 7/2018 | Noe et al. |
| 2018/0214263 A1 | 8/2018 | Rolando et al. |
| 2018/0243086 A1 | 8/2018 | Barbarino |
| 2018/0250126 A1 | 9/2018 | O'connor et al. |
| 2018/0250147 A1 | 9/2018 | Syed |
| 2018/0271654 A1 | 9/2018 | Hariton et al. |
| 2018/0280136 A1 | 10/2018 | Hariton et al. |
| 2018/0296333 A1 | 10/2018 | Dixon |
| 2018/0296336 A1 | 10/2018 | Cooper et al. |
| 2018/0296341 A1 | 10/2018 | Noe et al. |
| 2018/0325671 A1 | 11/2018 | Abunassar |
| 2018/0344457 A1 | 12/2018 | Gross et al. |
| 2018/0344490 A1* | 12/2018 | Fox .................... A61F 2/95 |
| 2018/0353294 A1 | 12/2018 | Calomeni et al. |
| 2019/0000613 A1 | 1/2019 | Delgado |
| 2019/0015200 A1 | 1/2019 | Delgado |
| 2019/0021852 A1 | 1/2019 | Delgado |
| 2019/0038404 A1 | 2/2019 | Iamberger et al. |
| 2019/0038405 A1 | 2/2019 | Iamberger et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083248 A1 | 3/2019 | Hariton et al. |
| 2019/0083249 A1 | 3/2019 | Hariton et al. |
| 2019/0083261 A1 | 3/2019 | Perszyk |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0192295 A1 | 6/2019 | Spence |
| 2019/0216602 A1 | 7/2019 | Lozonschi |
| 2019/0231525 A1 | 8/2019 | Hariton et al. |
| 2019/0336280 A1 | 11/2019 | Naor |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0038181 A1 | 2/2020 | Hariton et al. |
| 2020/0046496 A1 | 2/2020 | Hammer et al. |
| 2020/0060818 A1 | 2/2020 | Geist et al. |
| 2020/0146824 A1 | 5/2020 | Hammer et al. |
| 2020/0163760 A1 | 5/2020 | Hariton et al. |
| 2020/0163761 A1 | 5/2020 | Hariton et al. |
| 2020/0246140 A1 | 8/2020 | Hariton et al. |
| 2021/0093449 A1 | 4/2021 | Hariton et al. |
| 2021/0106419 A1 | 4/2021 | Abunassar |
| 2021/0113331 A1 | 4/2021 | Quadri |
| 2021/0137680 A1 | 5/2021 | Kizuka |
| 2021/0259835 A1 | 8/2021 | Tyler, II |
| 2022/0000612 A1 | 1/2022 | Hacohen |

FOREIGN PATENT DOCUMENTS

| | | |
|---|---|---|
| CN | 105324091 | 2/2016 |
| EP | 0170262 | 2/1986 |
| EP | 1264582 | 12/2002 |
| EP | 1637092 A2 | 3/2006 |
| EP | 1768630 | 1/2015 |
| EP | 2349124 B1 | 10/2018 |
| EP | 2739214 | 10/2018 |
| EP | 3583922 A1 | 12/2019 |
| EP | 3270825 B1 | 4/2020 |
| EP | 2485795 B1 | 9/2020 |
| GB | 844190 | 8/1960 |
| JP | S53152790 | 12/1978 |
| KR | 20010046894 | 6/2001 |
| WO | 1998/043557 | 10/1998 |
| WO | 1999/030647 | 6/1999 |
| WO | 2000-047139 | 8/2000 |
| WO | 2001-062189 | 8/2001 |
| WO | 01/82832 | 11/2001 |
| WO | 2003/028558 | 4/2003 |
| WO | 2004028399 A2 | 4/2004 |
| WO | 2004/108191 | 12/2004 |
| WO | 2005/107650 | 11/2005 |
| WO | 2006/007401 | 1/2006 |
| WO | 2006007389 A1 | 1/2006 |
| WO | 06/054930 | 5/2006 |
| WO | 2006/070372 | 7/2006 |
| WO | 2006/089236 | 8/2006 |
| WO | 2006128193 | 11/2006 |
| WO | 2007047488 A2 | 4/2007 |
| WO | 2007/059252 | 5/2007 |
| WO | 08/013915 | 1/2008 |
| WO | 2008/029296 | 3/2008 |
| WO | 2008/031103 | 3/2008 |
| WO | 2008/070797 | 6/2008 |
| WO | 2008/103722 | 8/2008 |
| WO | 09/033469 | 3/2009 |
| WO | 09/053497 | 4/2009 |
| WO | 2009/091509 | 7/2009 |
| WO | 2010/006627 | 1/2010 |
| WO | 2010027485 A1 | 3/2010 |
| WO | 2010/037141 | 4/2010 |
| WO | 2010/045297 | 4/2010 |
| WO | 2010/057262 | 5/2010 |
| WO | 2010/073246 | 7/2010 |
| WO | 2010/081033 | 7/2010 |
| WO | 2010/121076 | 10/2010 |
| WO | 2011/025972 | 3/2011 |
| WO | 2011/069048 | 6/2011 |
| WO | 2011/089601 | 7/2011 |
| WO | 2011/106137 | 9/2011 |
| WO | 2011/111047 | 9/2011 |
| WO | 01/87190 | 11/2011 |
| WO | 2011/137531 | 11/2011 |
| WO | 2011-143263 | 11/2011 |
| WO | 2011144351 A2 | 11/2011 |
| WO | 2011/154942 | 12/2011 |
| WO | 2012/011108 | 1/2012 |
| WO | 2012/024428 | 2/2012 |
| WO | 2012/036740 | 3/2012 |
| WO | 2012/048035 | 4/2012 |
| WO | 2012/127309 | 9/2012 |
| WO | 2012/177942 | 12/2012 |
| WO | 2013/021374 | 2/2013 |
| WO | 2013/021375 | 2/2013 |
| WO | 2013/021384 | 2/2013 |
| WO | 2013/059747 | 4/2013 |
| WO | 2013/072496 | 5/2013 |
| WO | 2013/078497 | 6/2013 |
| WO | 2013114214 | 8/2013 |
| WO | 2013/128436 | 9/2013 |
| WO | 2013/175468 | 11/2013 |
| WO | 2014/022124 | 2/2014 |
| WO | 2014/076696 | 5/2014 |
| WO | 2014/115149 | 7/2014 |
| WO | 2014121280 A2 | 8/2014 |
| WO | 2014/145338 | 9/2014 |
| WO | 2014144937 A2 | 9/2014 |
| WO | 2014/164364 | 10/2014 |
| WO | 2014/194178 | 12/2014 |
| WO | 2015/173794 | 11/2015 |
| WO | 2016/016899 | 2/2016 |
| WO | 2016/093877 | 6/2016 |
| WO | 2016/125160 | 8/2016 |
| WO | 2017/223486 | 12/2017 |
| WO | 2018/025260 | 2/2018 |
| WO | 2018/025263 | 2/2018 |
| WO | 2018/029680 | 2/2018 |
| WO | 2018/039631 | 3/2018 |
| WO | 2018/106837 | 6/2018 |
| WO | 2018/112429 | 6/2018 |
| WO | 2018/118717 | 6/2018 |
| WO | 2018/131042 | 7/2018 |
| WO | 2018/131043 | 7/2018 |
| WO | 2019/026059 | 2/2019 |

(56) References Cited

FOREIGN PATENT DOCUMENTS

| WO | 2019/030753 | 2/2019 |
|---|---|---|
| WO | 2019027507 | 2/2019 |
| WO | 2019/077595 | 4/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/165889 | 8/2020 |
| WO | 2021156866 A1 | 8/2021 |
| WO | 2021186424 A1 | 9/2021 |

OTHER PUBLICATIONS

An Invitation to pay additional fees dated May 19, 2021, which issued during the prosecution of Applicant's PCT/IL2021/050132.
An International Search Report and a Written Opinion both dated Jul. 12, 2021, which issued during the prosecution of Applicant's PCT/IL2021/050132.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021 (*Edwards Lifesciences* vs. *Cardiovalve*).
An Office Action dated Aug. 18, 2021, which issued during the prosecution of U.S. Appl. No. 17/210,183.
Institution decision dated Jul. 20, 2021 (*Edwards Lifesciences* vs. *Cardiovalve*).
Office Action (Notice of Allowance and Fees Due (PTOL-85)) dated Mar. 4, 2022 for U.S. Appl. No. 16/768,909 (pp. 1-29).
Office Action (Notice of Allowance and Fees Due (PTOL-85)) dated Mar. 22, 2022 for U.S. Appl. No. 17/366,711 (pp. 1-10).
Office Action (Notice of Allowance and Fees Due (PTOL-85)) dated Jan. 31, 2022 for U.S. Appl. No. 17/479,418 (pp. 1-194).
Office Action (Non-Final Rejection) dated Jan. 24, 2022 for U.S. Appl. No. 16/135,466 (pp. 1-8).
Office Action (Non-Final Rejection) dated Dec. 9, 2021 for U.S. Appl. No. 16/135,969 (pp. 1-11).
Office Action (Non-Final Rejection) dated Mar. 18, 2022 for U.S. Appl. No. 16/746,489 (pp. 1-9).
Office Action (Non-Final Rejection) dated Jan. 26, 2022 for U.S. Appl. No. 16/888,210 (pp. 1-7).
Office Action (Non-Final Rejection) dated Apr. 11, 2022 for U.S. Appl. No. 17/473,472 (pp. 1-7).
USPTO Before The Patent Trial and Appeal Board *Edwards Lifesciences Corporation and Edwards Lifesciences LLC*, Petitioner, v. *Cardiovalve Ltd.*, Patent Owner. IPR2021-00383 U.S. Pat. No. 10,226,341 B2, Preliminary Guidance Patent Owner's Motion to Amend, Entered: Jan. 31, 2022, (pp. 1-10).
International Search Report and Written Opinion issued in PCT/IL2018/051122 dated Jan. 25, 2019.
An Office Action dated Sep. 9, 2021, which issued during the prosecution of U.S. Appl. No. 16/768,909.
Notice of Allowance dated May 26, 2021, which issued during the prosecution of U.S. Appl. No. 16/135,599.
Office Action dated Oct. 14, 2021, which issued during the prosecution of U.S. Appl. No. 16/680,739.
An Office Action dated Oct. 21, 2021, which issued during the prosecution of U.S. Appl. No. 17/335,845.
European Search Report dated Oct. 11, 2021 which issued during the prosecution of Applicant's European App No. 21176010.3.
Fann, James I., et al. "Beating heart catheter-based edge-to-edge mitral valve procedure in a porcine model: efficacy and healing response." Circulation 110.8 (2004): 988-993.

Feldman, Ted, et al. "Percutaneous mitral repair with the MitraClip system: safety and midterm durability in the initial EVEREST (Endovascular Valve Edge-to-Edge Repair Study) cohort." Journal of the American College of Cardiology 54.8 (2009): 686-694.
IPR2021-00383 Patent Owner'S Contingent Motion to Amend Under 37 C.F.R. 42.121 dated Oct. 13, 2021.
IPR2021-00383 Patent Owner'S Response Pursuant To 37 C.F.R. 42.120 dated Oct. 13, 2021.
IPR2021-00383 Second Declaration of Dr. Michael Sacks dated Oct. 13, 2021.
An Office Action dated Oct. 21, 2021, which issued during the prosecution of U.S. Appl. No. 17/306,231.
Maisano, Francesco, et al. "The evolution from surgery to percutaneous mitral valve interventions: the role of the edge-to-edge technique." Journal of the American College of Cardiology 58.21 (2011): 2174-2182.
IPR2021-00383 Deposition of Dr. Ivan Vesely, dated Sep. 22, 2021.
Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
An Office Action dated Nov. 23, 2012, which issued during the prosecution of U.S. Appl. No. 13/033,852.
An Office Action dated Dec. 31, 2012, which issued during the prosecution of U.S. Appl. No. 13/044,694.
An Office Action dated Feb. 6, 2013, which issued during the prosecution of U.S. Appl. No. 13/412,814.
Langer F et al., "Ring plus String: Papillary muscle repositioning as an adjunctive repair technique for ischemic mitral regurgitation," J Thorac Cardiovasc Surg 133:247-9, Jan. 2007.
Langer F et al., "Ring+String: Successful repair technique for ischemic mitral regurgitation with severe leaflet tethering," Circulation 120[suppl 1]: S85-S91, Sep. 2009.
"Transcatheter Valve-in-Valve Implantation for Failed Bioprosthetic Heart Valves", J Webb et al., Circulation. Apr. 2010; 121: 1848-1857.
Jansen, J., Willeke, S., Reul, H. and Rum, G. (1992), Detachable Shape-Memory Sewing Ring for Heart Valves. Artificial Organs, 16:294-297. 1992 (an abstract).
Alexander S. Geha, et al., Replacement of degenerated mitral and aortic bioprostheses without explanation Ann Thorac Surg. Jun. 2001; 72:1509-1514.
An International Search Report and a Written Opinion both dated Oct. 13, 2011 which issued during the prosecution of Applicant's PCT/IL11/00231.
An Office Action dated Jul. 1, 2016, which issued during the prosecution of U.S. Appl. No. 14/161,921.
An International Search Report and a Written Opinion both dated Dec. 5, 2011, which issued during the prosecution of Applicant's PCT/IL11/00582.
An Office Action dated May 29, 2012, which issued during the prosecution of U.S. Appl. No. 12/840,463.
U.S. Appl. No. 61/555,160, filed Nov. 3, 2011.
U.S. Appl. No. 61/525,281, filed Aug. 19, 2011.
U.S. Appl. No. 61/537,276, filed Sep. 21, 2011.
U.S. Appl. No. 61/515,372, filed Aug. 5, 2011.
U.S. Appl. No. 61/492,449, filed Jun. 2, 2011.
U.S. Appl. No. 61/588,892, filed Jan. 20, 2012.
An International Search Report and a Written Opinion both dated Feb. 6, 2013, which issued during the prosecution of Applicant's PCT/IL12/00292.

(56) References Cited

OTHER PUBLICATIONS

An International Search Report and a Written Opinion both dated Feb. 6, 2013, which issued during the prosecution of Applicant's PCT/IL12/00293.
An Office Action dated Nov. 28, 2012, which issued during the prosecution of U.S. Appl. No. 12/961,721.
An Office Action dated Feb. 15, 2013, which issued during the prosecution of U.S. Appl. No. 12/840,463.
An Office Action dated Feb. 10, 2014, which issued during the prosecution of U.S. Appl. No. 13/033,852.
An Office Action dated Sep. 19, 2014, which issued during the prosecution of U.S. Appl. No. 13/044,694.
An International Search Report and a Written Opinion both dated Sep. 4, 2014 which issued durin the prosecution of Applicant's PCT/IL2014/050087.
Invitation to Pay Additional Fees dated Jun. 12, 2014 PCT/IL2014/050087.
An Office Action dated Jun. 17, 2014, which issued during the prosecution of U.S. Appl. No. 12/961,721.
An Office Action dated Jul. 3, 2014, which issued during the prosecution of U.S. Appl. No. 13/033,852.
An Office Action dated May 23, 2014, which issued during the prosecution of U.S. Appl. No. 13/412,814.
Dominique Himbert; Mitral Regurgitation and Stenosis from Bioprosthesis and Annuloplasty Failure: Transcatheter approaches and outcomes, 24 pages Oct. 28, 2013.
An International Search Report and a Written Opinion both dated Mar. 17, 2014 which issued during the prosecution of Applicant's PCT/IL2013/050937.
An International Preliminary Report on patentabilty dated Dec. 2, 2013, which issued during the prosecution of Applicant's PCT/IL11/00582.
An Office Action dated Sep. 12, 2013, which issued during the prosecution of U.S. Appl. No. 13/412,814.
An Office Action dated Aug. 2, 2013, which issued during the prosecution of U.S. Appl. No. 13/033,852.
An International Preliminary Report on patentabilty dated Sep. 11, 2012, which issued during the prosecution of Applicant's PCT/IL2011/000231.
An Office Action dated Jul. 2, 2014, which issued during the prosecution of U.S. Appl. No. 13/811,308.
An Office Action dated Jan. 20, 2016, which issued during the prosecution of U.S. Appl. No. 14/161,921.
An Office Action dated Jul. 23, 2013, which issued during the prosecution of U.S. Appl. No. 12/961,721.
An Office Action dated Jul. 18, 2013, which issued during the prosecution of U.S. Appl. No. 13/044,694.
An Office Action dated Nov. 8, 2013, which issued during the prosecution of U.S. Appl. No. 12/840,463.
An Office Action dated Jun. 4, 2014, which issued during the prosecution of U.S. Appl. No. 12/840,463.
An Office Action dated Aug. 13, 2012, which issued during the prosecution of U.S. Appl. No. 13/044,694.
An Office Action dated Jul. 2, 2012, which issued during the prosecution of U.S. Appl. No. 13/033,852.
An Office Action dated Feb. 3, 2014, which issued during the prosecution of U.S. Appl. No. 13/811,308.
An International Preliminary Report on patentabilty dated Feb. 11, 2014, which issued during the prosecution of Applicant's PCT/IL12/00292.
An International Preliminary Report on patentabilty dated Feb. 11, 2014, which issued during the prosecution of Applicant's PCT/IL12/00293.
A Notice of Allowance dated Aug. 15, 2014, which issued during the prosecution of U.S. Appl. No. 13/412,814.
An Office Action dated Aug. 14, 2012, which issued during the prosecution of U.S. Appl. No. 12/961,721.
U.S. Appl. No. 61/283,819, filed Dec. 8, 2009.
Notice of Allowance dated Apr. 8, 2016, which issued during the prosecution of U.S. Appl. No. 14/237,258.
U.S. Appl. No. 61/756,034, filed Jan. 24, 2013.
U.S. Appl. No. 61/756,049, filed Jan. 24, 2013.
An International Preliminary Report on Patentability dated Jan. 31, 2017, which issued during the prosecution of Applicant's PCT/IL2015/050792.
U.S. Appl. No. 62/372,861, filed Aug. 10, 2016.
Notice of Allowance dated Aug. 13, 2018, which issued during the prosecution of U.S. Appl. No. 15/995,597.
Notice of Allowance dated Apr. 20, 2018, which issued during the prosecution of U.S. Appl. No. 15/878,206.
An Office Action dated Dec. 10, 2015, which issued during the prosecution of U.S. Appl. No. 14/237,258.
An International Preliminary Report on Patentability dated Jul. 28, 2015, which issued during the prosecution of Applicant's PCT/IL2014/050087.
An Office Action dated Nov. 27, 2015, which issued during the prosecution of U.S. Appl. No. 14/626,267.
An Office Action dated Jan. 21, 2016, which issued during the prosecution of U.S. Appl. No. 14/237,264.
An Office Action dated Jan. 30, 2015, which issued during the prosecution of UK Patent Application No. 1413474.6.
An International Search Report and a Written Opinion both dated May 30, 2016, which issued during the prosecution of Applicant's PCT/IL2016/050125.
An Office Action dated Sep. 26, 2016, which issued during the prosecution of U.S. Appl. No. 14/763,004.
An Office Action dated Jan. 18, 2017, which issued during the prosecution of U.S. Appl. No. 14/626,267.
An Office Action dated Feb. 7, 2017, which issued during the prosecution of U.S. Appl. No. 14/689,608.
An Office Action dated Feb. 8, 2017, which issued during the prosecution of UK Patent Application No. 1613219.3.
An Office Action together dated Feb. 10, 2017, which issued during the prosecution of European Patent Application No. 12821522.5.
An International Search Report and a Written Opinion both dated Oct. 27, 2015, which issued during the prosecution of Applicant's PCT/IL2015/050792.
European Search Report dated Feb. 18, 2015, which issued during the prosecution of Applicant's European App No. 12821522.5.
Saturn Project—a novel solution for transcatheter heart valve replacement specifically designed to address clinical therapeutic needs on mitral valve: Dec. 2016.
Righini presentation EuroPCR May 2015 (Saturn)—(downloaded from: https://www.pcronline.com/Cases-resourcesimages/Resources/Course-videos-slides/2015/Cardiovascularinnovation-pipeline-Mitral-and-tricuspid-valve-interventions).
An Advisory Action dated Apr. 2, 2018, which issued during the prosecution of U.S. Appl. No. 14/763,004.
An Office Action dated Jul. 26, 2018, which issued during the prosecution of U.S. Appl. No. 15/872,501.
An Office Action dated May 4, 2018, which issued during the prosecution of U.S. Appl. No. 15/872,501.
An Office Action dated Apr. 20, 2018, which issued during the prosecution of U.S. Appl. No. 15/886,517.
An Office Action dated Aug. 9, 2018, which issued during the prosecution of U.S. Appl. No. 15/899,858.
An Office Action dated Aug. 9, 2018, which issued during the prosecution of U.S. Appl. No. 15/902,403.
An Office Action dated Jun. 28, 2018, which issued during the prosecution of Design U.S. Appl. No. 29/635,658.
An Office Action dated Jun. 28, 2018, which issued during the prosecution of Design U.S. Appl. No. 29/635,661.
Georg Lutter, MD, et al; "Percutaneous Valve Replacement: Current State and Future Prospects", The Annals of Thoracic Surgery ; vol. 78, pp. 2199-2206; Dec. 2004.
An Office Action dated Jun. 6, 2018, which issued during the prosecution of UK Patent Application No. 1720803.4.
U.S. Appl. No. 62/560,384, filed Sep. 19, 2017.
An International Search Report and a Written Opinion both dated Jun. 20, 2018, which issued during the prosecution of Applicant's PCT/IL2018/050024.
An Office Action dated Jun. 18, 2018, which issued during the prosecution of UK Patent Application No. 1800399.6.

(56) References Cited

OTHER PUBLICATIONS

An Office Action dated Oct. 23, 2017, which issued during the prosecution of U.S. Appl. No. 14/763,004.
An Office Action dated Dec. 7, 2017, which issued during the prosecution of U.S. Appl. No. 15/213,791.
Interview Summary dated Feb. 8, 2018, which issued during the prosecution of U.S. Appl. No. 15/213,791.
An Office Action dated Feb. 7, 2018, which issued during the prosecution of U.S. Appl. No. 15/197,069.
An International Search Report and a Written Opinion both dated Nov. 24, 2017, which issued during the prosecution of Applicant's PCT/IL2017/050873.
An Office Action dated Jan. 5, 2018, which issued during the prosecution of U.S. Appl. No. 15/541,783.
An Office Action dated Feb. 2, 2018, which issued during the prosecution of U.S. Appl. No. 15/329,920.
An Invitation to pay additional fees dated Jan. 2, 2018, which issued during the prosecution of Applicant's PCT/IL2017/050849.
An Invitation to pay additional fees dated Sep. 29, 2017, which issued during the prosecution of Applicant's PCT/IL2017/050873.
European Search Report dated Jun. 29, 2017, which issued during the prosecution of Applicant's European App No. 11809374.9.
An Invitation to pay additional fees dated Oct. 11, 2018, which issued during the prosecution of Applicant's PCT/IL2018/050725.
An Office Action dated Dec. 4, 2018, which issued during the prosecution of U.S. Appl. No. 16/045,059.
An Office Action together with the English translation dated Nov. 5, 2018 which issued during the prosecution of Chinese Patent Application No. 201680008328.5.
Notice of Allowance dated Sep. 25, 2018, which issued during the prosecution of U.S. Appl. No. 15/188,507.
European Search Report dated Sep. 26, 2018 which issued during the prosecution of Applicant's European App No. 18186784.7.
An Office Action dated Jun. 30, 2015, which issued during the prosecution of U.S. Appl. No. 14/522,987.
Notice of Allowance dated Dec. 13, 2013, which issued during the prosecution of U.S. Appl. No. 13/675,119.
An International Preliminary Report on Patentability dated Aug. 8, 2017, which issued during the prosecution of Applicant's PCT/IL2016/050125.
An Office Action dated Jan. 17, 2018, which issued during the prosecution of U.S. Appl. No. 14/763,004.
An Office Action dated Mar. 25, 2015, which issued during the prosecution of U.S. Appl. No. 12/840,463.
An Office Action dated Feb. 25, 2016, which issued during the prosecution of U.S. Appl. No. 14/522,987.
An Office Action dated Apr. 13, 2016, which issued during the prosecution of U.S. Appl. No. 14/626,267.
An Office Action dated Aug. 28, 2015, which issued during the prosecution of U.S. Appl. No. 14/237,264.
U.S. Appl. No. 62/112,343, filed Feb. 5, 2015.
Maisano (2015) TCR presentation re Cardiovalve.
Notice of Allowance dated Sep. 29, 2016, which issued during the prosecution of U.S. Appl. No. 14/442,541.
Notice of Allowance dated May 10, 2016, which issued during the prosecution of U.S. Appl. No. 14/237,258.
Notice of Allowance dated May 20, 2016, which issued during the prosecution of U.S. Appl. No. 14/237,258.
An International Preliminary Report on Patentability dated May 19, 2015, which issued during the prosecution of Applicant's PCT/IL2013/050937.
Dusan Pavcnik, MD, PhD2, et al; "Development and Initial Experimental Evaluation of a Prosthetic Aortic Valve for Transcatheter Placement", Cardiovascular Radiology. Radiology Apr. 1992, vol. 183, pp. 151-154.
Notice of Allowance dated Oct. 16, 2013, which issued during the prosecution of U.S. Appl. No. 13/675,119.
Notice of Allowance dated Feb. 11, 2015, which issued during the prosecution of U.S. Appl. No. 13/033,852.
Notice of Allowance dated May 5, 2015, which issued during the prosecution of U.S. Appl. No. 12/840,463.
Notice of Allowance dated Mar. 10, 2015, which issued during the prosecution of U.S. Appl. No. 13/811,308.
Notice of Allowance dated Jul. 1, 2016, which issued during the prosecution of U.S. Appl. No. 14/442,541.
An International Search Report and a Written Opinion both dated Nov. 9, 2018, which issued during the prosecution of Applicant's PCT/IL2018/050869.
An International Search Report and a Written Opinion both dated Dec. 5, 2018, which issued during the prosecution of Applicant's PCT/IL2018/050725.
An International Search Report and a Written Opinion both dated Apr. 25, 2019, which issued during the prosecution of Applicant's PCT/IL2019/050142.
An International Preliminary Report on Patentability dated Feb. 12, 2019, which issued during the prosecution of Applicant's PCT/IL2017/050873.
An Office Action dated Mar. 25, 2019, which issued during the prosecution of European Patent Application No. 14710060.6.
An International Search Report and a Written Opinion both dated Jan. 25, 2019, which issued during the prosecution of Applicant's PCT/IL2018/051122.
An International Search Report and a Written Opinion both dated May 13, 2019, which issued during the prosecution of Applicant's PCT/IL2018/051350.
An International Preliminary Report on Patentability dated Feb. 5, 2019, which issued during the prosecution of Applicant's PCT/IL2017/050849.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated Nov. 16, 2018, which issued during the prosecution of U.S. Appl. No. 16/042,028.
An Office Action dated Nov. 26, 2018, which issued during the prosecution of U.S. Appl. No. 16/040,831.
An Office Action dated Jul. 11, 2018, which issued during the prosecution of U.S. Appl. No. 15/978,494.
An Office Action dated Nov. 23, 2018, which issued during the prosecution of U.S. Appl. No. 16/041,208.
An Office Action dated Jun. 15, 2018, which issued during the prosecution of U.S. Appl. No. 15/970,314.
An Office Action dated Oct. 12, 2018, which issued during the prosecution of U.S. Appl. No. 15/970,314.
An Office Action dated Jul. 26, 2018, which issued during the prosecution of U.S. Appl. No. 15/979,686.
An Office Action dated Sep. 10, 2018, which issued during the prosecution of U.S. Appl. No. 16/008,618.
An Office Action dated Sep. 6, 2018, which issued during the prosecution of U.S. Appl. No. 15/994,022.
An Office Action dated Sep. 7, 2018, which issued during the prosecution of U.S. Appl. No. 15/995,725.
An Office Action dated Aug. 1, 2019, which issued during the prosecution of U.S. Appl. No. 15/668,559.
An Office Action dated Apr. 22, 2019, which issued during the prosecution of U.S. Appl. No. 15/668,559.
An Office Action dated Jun. 19, 2019, which issued during the prosecution of U.S. Appl. No. 15/682,789.
Notice of Allowance dated Aug. 30, 2019, which issued during the prosecution of U.S. Appl. No. 15/682,789.
Notice of Allowance dated Mar. 29, 2019, which issued during the prosecution of U.S. Appl. No. 15/541,783.

(56) References Cited

OTHER PUBLICATIONS

Sündermann, Simon H., et al. "Feasibility of the Engager™ aortic transcatheter valve system using a flexible over-the-wire design." European Journal of Cardio-Thoracic Surgery 42.4 (2012): e48-e52.
An Office Action summarized English translation and Search Report dated Jul. 3, 2020, which issued during the prosecution of Chinese Patent Application No. 201780061210.3.
An Office Action dated May 16, 2019, which issued during the prosecution of U.S. Appl. No. 15/433,547.
An Office Action dated Jun. 25, 2019, which issued during the prosecution of U.S. Appl. No. 15/329,920.
An Office Action dated Nov. 18, 2019, which issued during the prosecution of U.S. Appl. No. 17/752,184.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Aug. 16, 2019, which issued during the prosecution of U.S. Appl. No. 15/668,659.
An Office Action dated Nov. 1, 2019, which issued during the prosecution of U.S. Appl. No. 15/872,501.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Jun. 13, 2019, which issued during the prosecution of U.S. Appl. No. 16/388,038.
An Office Action dated Dec. 31, 2019, which issued during the prosecution of U.S. Appl. No. 16/591,330.
An Office Action dated Jan. 6, 2020, which issued during the prosecution of U.S. Appl. No. 16/660,231.
An Office Action dated May 11, 2018, which issued during the prosecution of U.S. Appl. No. 15/899,858.
An Office Action dated Dec. 31, 2019, which issued during the prosecution of U.S. Appl. No. 16/183,140.
An Office Action dated May 8, 2018, which issued during the prosecution of U.S. Appl. No. 15/902,403.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action dated Aug. 7, 2020, which issued during the prosecution of U.S. Appl. No. 15/668,659.
An Office Action dated Jul. 14, 2020, which issued during the prosecution of U.S. Appl. No. 16/324,339.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=FLzLBQAAQBAJ&lpg=PA198&ots=soqWrDH-y_&dg=%20%22Edwards%20SAPIEN%22&lr&pg=PA20#v=onepage&q=%22Edwards%20SAPIEN%22&f=false ; Downloaded on Jun. 18, 2020.
U.S. Appl. No. 62/139,854, filed Mar. 30, 2015.
An Advisory Action dated Jan. 2, 2020, which issued during the prosecution of U.S. Appl. No. 15/668,659.
An Office Action summarized English translation and Search Report dated Nov. 25, 2020, which issued during the prosecution of Chinese Patent Application No. 201910449820.1.
Notice of Allowance dated Nov. 19, 2020, which issued during the prosecution of U.S. Appl. No. 16/318,025.
An International Search Report and a Written Opinion both dated Jun. 24, 2020, which issued during the prosecution of Applicant's PCT/IL2019/051398.
Notice of Allowance dated Aug. 28, 2020, which issued during the prosecution of U.S. Appl. No. 16/324,339.
Notice of Allowance dated Sep. 10, 2020, which issued during the prosecution of U.S. Appl. No. 16/324,339.
Notice of Allowance dated Oct. 5, 2018, which issued during the prosecution of U.S. Appl. No. 15/886,517.
An Office Action dated Oct. 5, 2020, which issued during the prosecution of Canadian Patent Application No. 2,973,940.
An Office Action dated Aug. 29, 2018, which issued during the prosecution of U.S. Appl. No. 15/329,920.
Notice of Allowance dated Oct. 17, 2019, which issued during the prosecution of U.S. Appl. No. 15/329,920.
Notice of Allowance dated Apr. 27, 2020, which issued during the prosecution of U.S. Appl. No. 16/591,330.
An Office Action dated Sep. 29, 2017, which issued during the prosecution of U.S. Appl. No. 15/197,069.
Notice of Allowance dated May 22, 2017, which issued during the prosecution of U.S. Appl. No. 14/689,608.
An Office Action dated Sep. 24, 2020, which issued during the prosecution of U.S. Appl. No. 16/811,732.
An International Preliminary Report on Patentability dated Oct. 20, 2020, which issued during the prosecution of Applicant's PCT/IL2019/050142.
An Office Action dated Nov. 30, 2020, which issued during the prosecution of U.S. Appl. No. 16/138,129.
Notice of Allowance dated Aug. 18, 2017 which issued during the prosecution of U.S. Appl. No. 14/689,608.
Notice of Allowance dated Jul. 6, 2017, which issued during the prosecution of U.S. Appl. No. 14/689,608.
An Office Action dated Apr. 21, 2017, which issued during the prosecution of U.S. Appl. No. 15/213,791.
Symetis S.A.: "Acurate neo™ Aortic Bioprosthesis for Implantation using the Acurate neo™ TA Transapical Delivery System in Patients with Severe Aortic Stenosis," Clinical Investigation Plan, Protocol No. 2015-01, Vs. No. 2, 2015:1-76.
Tchetche, D. and Nicolas M. Van Mieghem: "New-generation TAVI devices: description and specifications" EuroIntervention, 2014, No. 10:U90-U100.
An Office Action dated Jul. 29, 2020, which issued during the prosecution of U.S. Appl. No. 16/132,937.
Notice of Allowance dated May 7, 2020, which issued during the prosecution of U.S. Appl. No. 16/637,166.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
Notice of Allowance dated Sep. 10, 2020, which issued during the prosecution of U.S. Appl. No. 15/600,190.
U.S. Appl. No. 62/030,715, filed Jul. 30, 2014.
Notice of Allowance dated Jul. 19, 2019, which issued during the prosecution of U.S. Appl. No. 15/899,858.
An International Search Report and a Written Opinion both dated Mar. 27, 2018, which issued during the prosecution of Applicant's PCT/IL2017/050849.
U.S. Appl. No. 61/312,412, filed Mar. 10, 2010.
An International Preliminary Report on patentabilty dated Jun. 16, 2020, which issued during the prosecution of Applicant's PCT/IL2018/051350.
An Office Action dated Aug. 13, 2019, which issued during the prosecution of UK Patent Application No. 1901887.8.
An Invitation to pay additional fees dated Mar. 14, 2019, which issued during the prosecution of Applicant's PCT/IL2018/051350.
Ex Parte Quayle issued in U.S. Appl. No. 16/879,952, dated May 2, 2022, 10 pages.

(56) References Cited

OTHER PUBLICATIONS

USPTO Before the Patent Trial and Appeal Board *Edwards Lifesciences Corp and Edwards Lifesciences LLC* v. *Cardiovalve Ltd.*, IPR2021-01051, U.S. Pat. No. 10,702,385B2, Preliminary Guidance Patent Owner's Motion to Amend, dated Jun. 24, 2022, 22 pages.
International Search Report issued in App. No. PCT/IL2021/051433, dated May 3, 2022, 24 pages.
Notice of Allowance issued in U.S. Appl. No. 16/680,739, dated May 4, 2022, 8 pages.
Chinese Office Action (with English translation) issued in App. No. CN201880058940.2, dated May 7, 2022, 13 pages.
Final Office Action issued in U.S. Appl. No. 16/135,969, dated Jun. 28, 2022, 24 pages.
Final Office Action issued in U.S. Appl. No. 16/144,054, dated Jul. 8, 2022, 45 pages.
Final Decision in IPR2021-00383 dated Jul. 18, 2022, 96 pages.
Petitioners' Opposition to Patent Owner's Contingent Motion to Amend, Filed Jan. 5, 2022, *Edwards Lifesciences Corporation and Edwards Lifesciences LLC* v. *Cardiovalve Ltd.*, IPR2021-00383, 32 pages.
Petitioners' Reply to Patent Owner's Reponse, Filed Jan. 5, 2022, *Edwards Lifesciences Corporation and Edwards Lifesciences LLC* v. *Cardiovalve Ltd.*, IPR2021-00383, 41 pages.
Notice of Allowance dated Dec. 6, 2021, issued for U.S. Appl. No. 16/738,516, 30 pages.
Notice of Allowance dated Dec. 29, 2021, issued for U.S. Appl. No. 17/210,183, 13 pages.
Notice of Allowance dated Dec. 7, 2021, issued for U.S. Appl. No. 17/394,807,115 pages.
Non-Final Office Action dated Jan. 12, 2022, issued for U.S. Appl. No. 17/101,787, 17 pages.
European Patent Office Communication pursuant to Rule 164(2)(b) and Article 94(3) EPC for App. No. EP18826823.9, dated Nov. 25, 2021, 14 pages.
European Patent Office Communication pursuant to Article 94(3) EPC for App. No. EP20714289.4, dated Sep. 22, 2021, 5 pages.
Decision Granting Institution of Inter Partes Review 35 USC §314, dated Dec. 10, 2021, *Edwards Lifesciences Corporation and Edwards Lifesciences LLC* v. *Cardiovalve Ltd.*, IPR2021-00383, 42 pages.
English translation of Chinese Office Action issued for CN201880064313.X, dated Jan. 6, 2022, 3 pages.
Fucci, C., et al. "Improved results with mitral valve repair using new surgical techniques." European journal of cardio-thoracic surgery 9.11 (1995): 621-627.
Poirier, Nancy C., et al. "A novel repair for patients with atrioventricular septal defect requiring reoperation for left atrioventricular valve regurgitation." European journal of cardio-thoracic surgery 18.1 (2000): 54-61.
An Office Action dated Mar. 29, 2021, which issued during the prosecution of U.S. Appl. No. 16/738,516.
Ando, Tomo, et al. "Iatrogenic ventricular septal defect following transcatheter aortic valve replacement: a systematic review." Heart, Lung and Circulation 25.10 (2016): 968-974.
Urena, Marina, et al. "Transseptal transcatheter mitral valve replacement using balloon-expandable transcatheter heart valves: a step-by-step approach." JACC: Cardiovascular Interventions 10.19 (2017): 1905-1919.
An English summary of an Official Action dated Mar. 29, 2021, which issued during the prosecution of Chinese Patent Application No. 201780061210.3.
An International Search Report and a Written Opinion both dated Jan. 28, 2020, which issued during the prosecution of Applicant's PCT/IL2019/051031.
An International Preliminary Report on Patentability dated Mar. 9, 2021, which issued during the prosecution of Applicant's PCT/IL2019/051031.
An Office Action dated May 4, 2021, which issued during the prosecution of U.S. Appl. No. 16/636,204.
Notice of Allowance dated May 17, 2021, which issued during the prosecution of U.S. Appl. No. 16/138,129.
Notice of Allowance dated Jun. 4, 2021, which issued during the prosecution of U.S. Appl. No. 16/802,353.
An Office Action dated May 12, 2021, which issued during the prosecution of Canadian Patent Application No. 2,973,940.
Petition for Inter Partes Rreview of U.S. Pat. No. 10,702,385— dated Jun. 4, 2021.
Declaration of Ivan Vesely, Ph.D. In Support of Petition for Inter Partes Review of U.S. Pat. No. 10,702,385—dated Jun. 4, 2021.
Maisano, F., et al. "The edge-to-edge technique: a simplified method to correct mitral insufficiency." European journal of cardio-thoracic surgery 13.3 (1998): 240-246.
An Office Action dated Dec. 24, 2020, which issued during the prosecution of U.S. Appl. No. 16/144,054.
An Office Action dated Feb. 2, 2021, which issued during the prosecution of U.S. Appl. No. 16/811,732.
An Office Action together with an English summary dated Mar. 3, 2021, which issued during the prosecution of Chinese Patent Application No. 201780047391.4.
An Office Action dated Jan. 13, 2021, which issued during the prosecution of European Patent Application No. 15751089.2.
An Office Action dated Jul. 27, 2022, which issued during the prosecution of U.S. Appl. No. 16/881,350. 176 pages.
An Office Action dated Sep. 21, 2022, which issued during the prosecution of U.S. Appl. No. 16/776,581. 142 pages.
An Office Action dated Jul. 20, 2022, which issued during the prosecution of U.S. Appl. No. 17/101,787. 26 pages.
An Office Action dated Sep. 16, 2022, which issued during the prosecution of U.S. Appl. No. 16/135,466. 19 pages.
An Office Action dated Aug. 1, 2022, which issued during the prosecution of European Patent Application No. 18826823.9. 5 pages.
European Search Report dated Sep. 6, 2022 which issued during the prosecution of Applicant's European App No. 22161862.2. 6 pages.
IPR2021-01051 Petitioners' Reply to Preliminary Guidance dated Aug. 2, 2022, 17 pages.
IPR2021-01051 Patent Owner'S Sur-Reply to Petitioners' Reply to Preliminary Guidance dated Aug. 23, 2022, 10 pages.
An Office Action dated Sep. 8, 2022, which issued during the prosecution of U.S. Appl. No. 16/896,858. 116 pages.

* cited by examiner

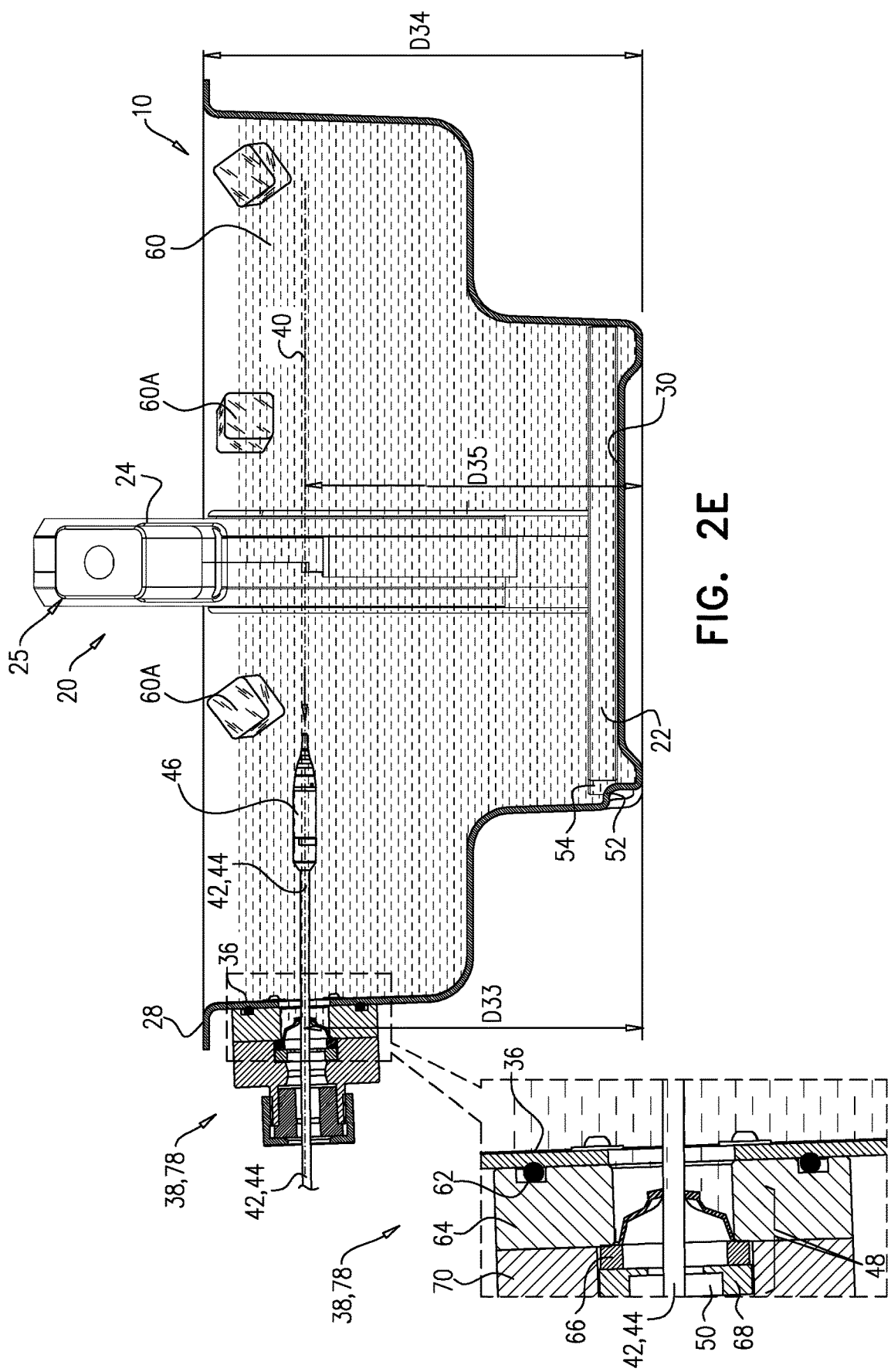

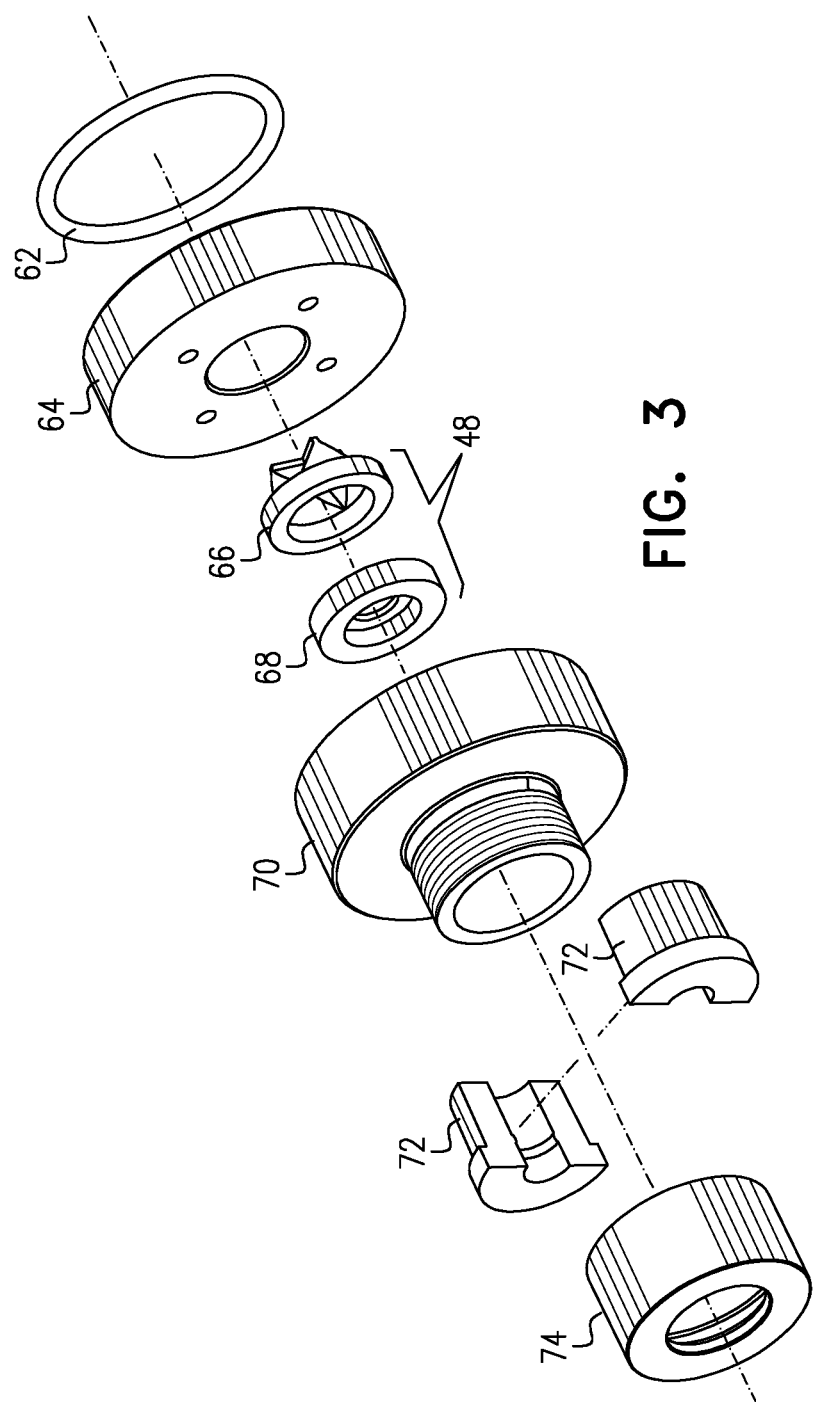

TEMPERATURE-CONTROL DURING CRIMPING OF AN IMPLANT

CROSS-REFERENCES TO RELATED APPLICATIONS

The present application is the US National Phase of PCT application IL2018/051122 to Karalnik et al., filed Oct. 21, 2018, and entitled "TEMPERATURE-CONTROL DURING CRIMPING OF AN IMPLANT," which published as WO 2019/138400, and which claims priority from UK patent application GB 1800399.6, filed Jan. 10, 2018, and entitled "TEMPERATURE-CONTROL DURING CRIMPING OF AN IMPLANT," which is incorporated herein by reference.

FIELD OF THE INVENTION

Some applications of the present invention relate in general to the application of heat-transfer fluid to workpieces during their preparation. More specifically, some applications of the present invention relate to the cooling of a Nitinol frame of a prosthetic heart valve or vascular stent during crimping.

BACKGROUND

The use of shape memory alloys (SMAs) has been widely adopted in a range of medical devices. SMAs possess shape memory as a result of the alloy undergoing a reversible temperature-dependent transformation between an austenite molecular structure and a martensite molecular structure. Thus, SMA-based medical devices may possess shape memory in that they can be reformed from an original, austenitic configuration to a second, martensitic configuration by lowering their temperature, and subsequently restored to their original austenitic configuration, by elevating their temperature. Importantly, when an SMA device, in its original shape and size, is cooled to its martensitic state, and subsequently deformed, it will retain its deformed shape and size. Upon warming of the SMA device to its austenitic state, the device will recover its original shape and size.

The use of SMAs has been shown to be particularly useful in the context of implants percutaneously implanted into a patient's cardiovascular system, including prosthetic heart valves. Due to the relatively narrow diameter of the vascular system via which prosthetic heart valves are frequently delivered, it is often desirable to deliver the implant in a crimped state, achieved while the implant is in its martensitic configuration. When the implant is exposed to physiological temperatures, the implant undergoes transformation to its austenitic configuration. The thermoelastic expansion enabled by the implant's transformation to its austenitic configuration may be controlled mechanically by housing the implant within a sleeve of a delivery tool. The regulated release of the implant from the housing enables the gradual return of the implant to its original shape and size upon delivery to the desired anatomical location.

SUMMARY OF THE INVENTION

The present invention is directed to apparatus and methods for temperature control during crimping of a medical implant.

When an SMA device, in its original shape and size, is cooled to its martensitic state, and subsequently deformed, it will retain its deformed shape and size. Upon warming of the SMA device to its austenitic state, the device will recover its original shape and size. Since implants comprising SMAs, such as nickel titanium (Nitinol), are more easily deformed while in their martensitic state, it is therefore desirable to crimp such an implant while cooled below its transition temperature. Such crimping of a cooled SMA implant reduces a likelihood of damaging the implant or delivery tool during the crimping and loading processes.

Aspects of the present invention include apparatus and methods for crimping a frame of an SMA implant while the SMA implant is at least partially submerged in a cooled liquid that maintains the SMA implant in its martensitic state. The submersion of the frame of an SMA implant during crimping is achieved by disposition of a crimping device within a bath of the cooled liquid.

Some aspects of the present invention include alignment of the crimping aperture with a port in a side-wall of the bath, enabling advancing a delivery tool that comprises a shaft and a housing at a distal end of the shaft, housing-first, through the port, at least until the housing reaches the aperture, crimping the frame onto the delivery tool by actuating the crimping mechanism.

Other aspects of the present invention include a seal configured to maintain sealing as the housing and the shaft pass through the port during the advancing.

There is therefore provided, in accordance with an application of the present invention, apparatus for crimping a frame of an implant, the apparatus including:

a crimping device including (i) a base, and (ii) a crimping mechanism that defines a crimping aperture;

a bath having a floor, the bath (i) defining a receptacle that is shaped to receive a portion of the crimping device, and (ii) having one or more side-walls, the one or more side-walls:
  extending upward from the floor to a side-wall height, and
  including a port-defining side-wall, wherein the port-defining side-wall defines a port between outside of the bath and inside of the bath;
the apparatus having an assembled state in which the portion of the crimping device has been received by the receptacle,
wherein, in the assembled state:
  the crimping device is held securely by the bath,
  the aperture is below the side-wall height, and
  the port is aligned with the crimping aperture.

In an application, the crimping mechanism has a thickness, and the bath has an internal width that is 16-24 cm greater than the thickness of the crimping mechanism.

In an application, the receptacle is a recess, configured to snugly receive the portion of the crimping device.

In an application, the bath defines the recess in the floor, and the recess is shaped to receive at least a portion of the base.

In an application, in the assembled state, a height of the aperture is within 1 cm of a height of the port.

In an application, the bath is shaped to receive the crimping device in a pre-defined rotational orientation of the crimping device with respect to the bath.

In an application, in the pre-defined rotational orientation, a rotational position of the aperture is within 5 degrees of a rotational position of the port.

In an application, the receptacle and the portion of the crimping device are cooperatively shaped to inhibit, in the assembled state, rotation of the crimping device out of the pre-defined rotational orientation.

In an application:

a first element selected from the group consisting of: the receptacle, and the portion of the crimping device is shaped to define a protrusion, another element selected from the group is shaped to define a notch, and the protrusion and the notch inhibit the rotation of the crimping device out of the pre-defined rotational orientation by, in the assembled state, the protrusion being disposed within the notch.

In an application, the port defines a channel, and includes a seal that reversibly closes the channel.

In an application, the channel has an internal diameter of 6-15 mm.

In an application, the apparatus includes a delivery tool that includes a shaft and a housing at a distal end of the shaft, the delivery tool being advanceable, housing-first, through the port, at least until the housing reaches the aperture, and the seal is configured to maintain sealing as the housing and the shaft pass through the port during the advancing.

In an application:

the port includes an external portion outside of the bath, the external portion of the port is dimensioned such that, while the shaft extends through the port, an annular gap is defined around the shaft, between the shaft and the external portion of the port, the apparatus further includes a cap and a plurality of plugs, the cap (i) defines an opening through which the housing is advanceable, and (ii) is securable to the external portion of the port, the plurality of plugs are shaped to be formable into a ring that circumscribes the shaft, and that fits snugly within in the gap.

In an application, the external portion of the port defines a screw thread, the cap defines a complementary screw thread, and the cap is securable to the external portion of the port by being screwed onto the external portion of the port.

In an application, the apparatus includes an implant, the implant including a tubular frame that: (i) circumscribes a longitudinal axis, (ii) defines a radial diameter, and (iii) has a crimped state and a non-crimped state, in which the radial diameter of the frame in the crimped state is smaller than the radial diameter of the frame in the non-crimped state.

In an application, the implant is a prosthetic heart valve or vascular stent.

In an application:

the crimping mechanism has a first side and first side, and the bath has an internal width sufficient to allow a human operator to simultaneously place a first hand inside the bath on the first side of the crimping mechanism, and a second hand inside the bath on the second side of the crimping mechanism.

In an application:

the crimping aperture has an open state and a narrowed state, the crimping device further includes a handle, the crimping mechanism being actuatable by moving the handle circumferentially around the crimping mechanism, and actuation of the crimping mechanism transitions the crimping aperture from its open state to its narrowed state.

In an application:

the crimping device has a working diameter, defined between a first position of an end of the handle when the crimping aperture is in its open state, and a second position of the end of the handle when the aperture is in its narrowed state, and the bath has an internal width that is greater than the working diameter.

In an application, the internal width of the bath is less than 5 cm greater than the working diameter of the crimping device.

In an application, the internal width of the bath is less than 2 cm greater than the working diameter of the crimping device.

In an application, the internal width of the bath is 1-10 mm greater than the working diameter of the crimping device.

In an application, the handle is below the side-wall height in both the open state and the narrowed state.

In an application, during transitioning of the crimping aperture from its open state to its narrowed state, the handle is temporarily elevated above the side-wall height.

There is further provided, in accordance with an application of the present invention, apparatus for crimping a frame of an implant, the apparatus including a crimping assembly, the crimping assembly including:

a bath having a floor, and one or more side-walls extending upward from the floor to a side-wall height; and a crimping mechanism that defines a crimping aperture, the crimping mechanism attached to the bath such that the crimping aperture is disposed within the bath below the side-wall height.

In an application, the one or more side-walls include a port-defining side-wall, and the port-defining side-wall defines a port between outside of the bath and inside of the bath, the port being aligned with the crimping aperture of the crimping device.

In an application, an aperture-height of the aperture is within 1 cm of a port-height of the port.

In an application, a rotational position of the aperture is within 5 degrees of a rotational position of the port.

In an application, the port defines a channel, and includes a seal that reversibly closes the channel.

In an application, the channel has an internal diameter of 6-15 mm.

In an application, the apparatus includes a delivery tool that includes a shaft and a housing at a distal end of the shaft, the delivery tool being advanceable, housing-first, through the port, at least until the housing reaches the aperture, and the seal is configured to maintain sealing as the housing and the shaft pass through the port during the advancing.

In an application:

the port includes an external portion outside of the bath, the external portion of the port is dimensioned such that, while the shaft extends through the port, an annular gap is defined around the shaft, between the shaft and the external portion of the port, the apparatus further includes a cap and a plurality of plugs, the cap (i) defines an opening through which the housing is advanceable, and (ii) is securable to the external portion of the port, the plurality of plugs are shaped to be formable into a ring that circumscribes the shaft, and that fits snugly within in the gap.

In an application, the external portion of the port defines a screw thread, the cap defines a complementary screw thread, and the cap is securable to the external portion of the port by being screwed onto the external portion of the port.

In an application, the apparatus includes an implant, the implant including a tubular frame that: (i) circumscribes a longitudinal axis, (ii) defines a radial diameter, and (iii) has a crimped state and a non-crimped state, in which the radial diameter of the frame in the crimped state is smaller than the radial diameter of the frame in the non-crimped state.

In an application, the implant is a prosthetic heart valve or vascular stent.

In an application:
the crimping mechanism has a first side and first side, and
the bath has an internal width sufficient to allow a human operator to simultaneously place a first hand inside the bath on the first side of the crimping mechanism, and a second hand inside the bath on the second side of the crimping mechanism.

In an application, the crimping mechanism has a thickness, and the bath has an internal width that is 16-24 cm greater than the thickness of the crimping mechanism.

In an application:
the crimping aperture has an open state and a narrowed state,
the crimping device further includes a handle, the crimping mechanism being actuatable by moving the handle circumferentially around the crimping mechanism, and
actuation of the crimping mechanism transitions the crimping aperture from its open state to its narrowed state.

In an application:
the crimping device has a working diameter, defined between a first position of an end of the handle when the crimping aperture is in its open state, and a second position of the end of the handle when the aperture is in its narrowed state, and
the bath has an internal width that is greater than the working diameter.

In an application, the internal width of the bath is less than 5 cm greater than the working diameter of the crimping device.

In an application, the internal width of the bath is less than 2 cm greater than the working diameter of the crimping device.

In an application, the internal width of the bath is 1-10 mm greater than the working diameter of the crimping device.

In an application, the handle is below the side-wall height in both the open state and the narrowed state.

In an application, during transitioning of the crimping aperture from its open state to its narrowed state, the handle is temporarily elevated above the side-wall height.

There is further provided, in accordance with an application of the present invention, method for crimping an expandable frame, the method including:
introducing a cooled liquid into a bath, the bath having a floor and one or more side-walls, at least one of the side-walls being a port-defining side-wall that defines a port from inside the bath to outside the bath;
inserting at least a part of a delivery tool through the port into the bath,
inserting the expandable frame, disposed on the part of the delivery tool, to a crimping aperture of a crimping mechanism disposed within and coupled to the bath; and
while (i) the frame remains disposed within the aperture, and (ii) the frame is at least partially submerged in the liquid, crimping the frame onto the delivery tool by actuating the crimping mechanism.

In an application, introducing the cooled liquid into the bath includes introducing the cooled liquid into the bath while the liquid has a temperature of between −2 and 12 degrees C.

In an application, the method includes introducing, into the bath, a frozen portion of the liquid.

In an application, the method includes, prior to crimping the frame, immersing the frame in the cooled liquid in the bath for at least 10 seconds.

In an application, the method includes, prior to crimping the frame, immersing the frame in the cooled liquid in the bath for between 30 seconds and 10 minutes.

In an application, the crimping mechanism has a first side and a second side, and inserting the expandable frame includes manually inserting the frame to within the crimping aperture facilitated by placing a first hand within the bath on the first side of the crimping mechanism, and a second hand within the bath on the second side of the crimping mechanism.

In an application, actuating the crimping mechanism includes revolving a handle about halfway circumferentially around the crimping mechanism, and revolving the handle causes transitioning of the crimping aperture from an open state to a narrowed state.

In an application, the method includes, prior to revolving the handle, grasping the handle while aperture is in its open state and the handle is disposed in the liquid.

In an application, actuating the crimping mechanism includes transitioning the crimping aperture into the narrowed state by revolving the handle such that the handle enters the liquid.

In an application, the port includes an external portion outside of the bath, and the method further includes:
prior to inserting the part of the delivery tool through the port into the bath, passing the part of the delivery tool through a cap; and
subsequently to inserting the part of the delivery tool through the port into the bath, fastening the cap to the external portion of the port.

In an application:
the delivery tool includes a shaft,
inserting at least the part of the delivery tool through the port into the bath includes positioning the shaft through the port,
the method further includes, prior to securing the cap to the external portion of the port, arranging a plurality of plugs into a ring that circumscribes the shaft and is disposed in a gap between the shaft and the external portion of the port, and
fastening the cap to the external portion of the port includes securing the ring of plugs within the gap.

In an application, fastening the cap to the external portion of the port includes screwing the cap onto the external portion of the port, sealing the port.

In an application, screwing the cap onto the external portion of the port further includes pushing the plurality of plugs into the gap between the shaft and the external portion of the port.

In an application, the method includes forming a crimping assembly in which the crimping mechanism is held securely within the bath, and the crimping aperture is below the side-wall height, by placing the crimping device into the bath, and coupling the crimping device to the bath.

In an application, forming the crimping assembly includes coupling the crimping device to the bath such that the port is aligned with the aperture.

In an application, forming the crimping assembly includes coupling the crimping device to the bath such that a rotational position of the aperture is within 5 degrees of a rotational position of the port.

In an application, forming the crimping assembly includes coupling the crimping device to the bath such that an aperture-height of the aperture is within 1 cm of a port-height of the port.

In an application, the method includes threading the frame onto the part of the delivery tool.

In an application, threading the frame onto the part of the delivery tool includes threading the frame onto the part of the delivery tool subsequently to inserting the part of the delivery tool through the port into the bath.

There is further provided, in accordance with an application of the present invention, apparatus for crimping a frame of an implant, the apparatus including:

a crimping device including (i) a base, and (ii) a crimping mechanism that defines a crimping aperture;

a bath having a floor, the bath (i) defining a receptacle that is shaped to receive a portion of the crimping device, and (ii) having one or more side-walls, the one or more side-walls:

extending upward from the floor to a side-wall height, and including a port-defining side-wall, wherein the port-defining side-wall defines a port between outside of the bath and inside of the bath;

the apparatus having an assembled state in which the portion of the crimping device has been received by the receptacle, wherein, in the assembled state:

the crimping device is held securely by the bath, the aperture is below the side-wall height, and the port is aligned with the crimping aperture.

The present invention will be more fully understood from the following detailed description of applications thereof, taken together with the drawings, in which:

BRIEF DESCRIPTION OF THE DRAWINGS

FIGS. 2A-E are schematic illustrations showing a crimping assembly being used in combination with a delivery tool to crimp a frame of an implant, in accordance with some applications of the invention;

FIG. 3 is a schematic illustration of a seal connected by a cap to an external portion of a port, in accordance with some applications of the invention;

DETAILED DESCRIPTION OF EMBODIMENTS

Figure 1A:
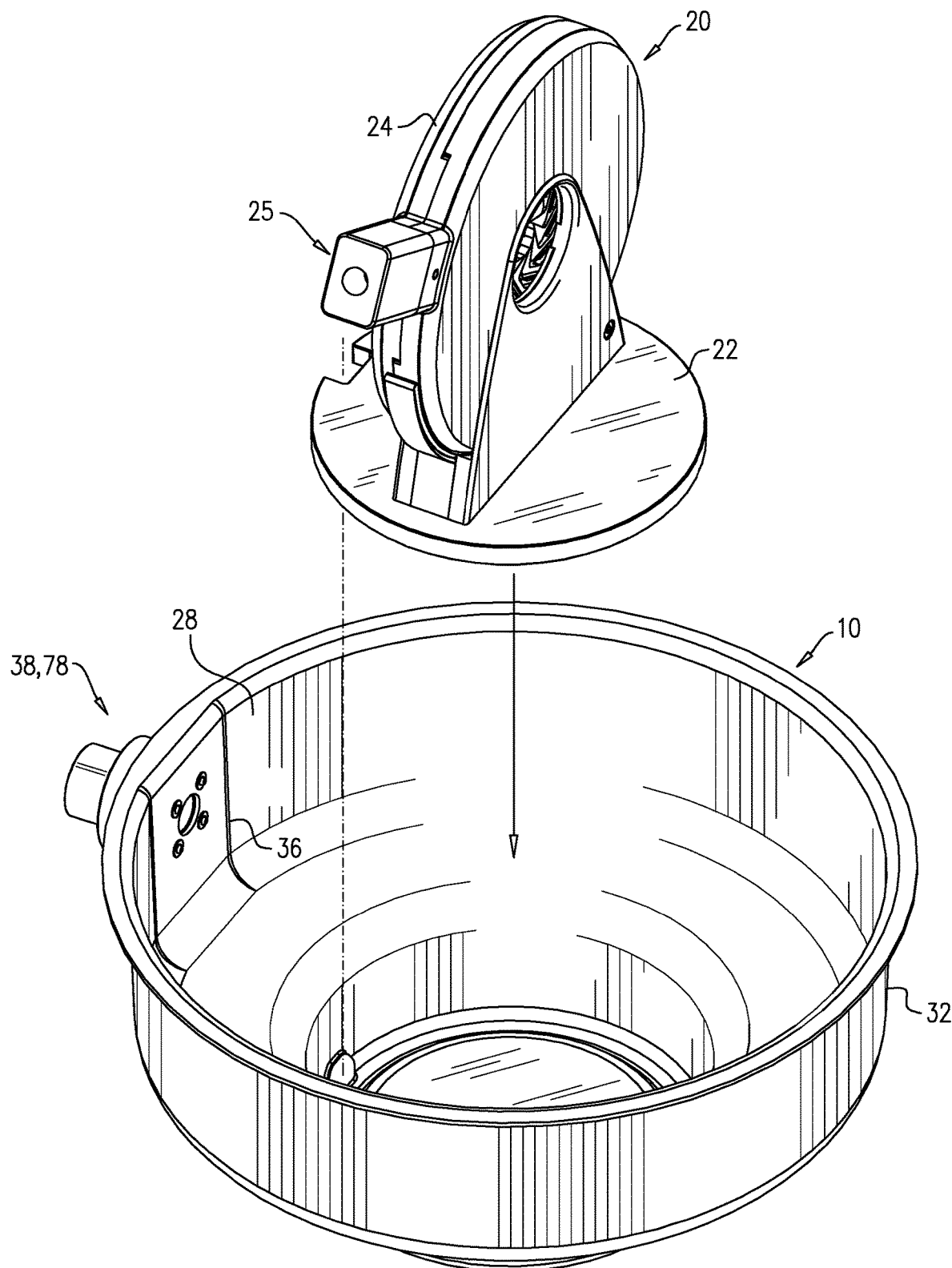
FIGS. 1A-C are schematic illustrations of a crimping assembly, comprising a crimping device and a bath, in accordance with some applications of the invention.
Figure 1B:
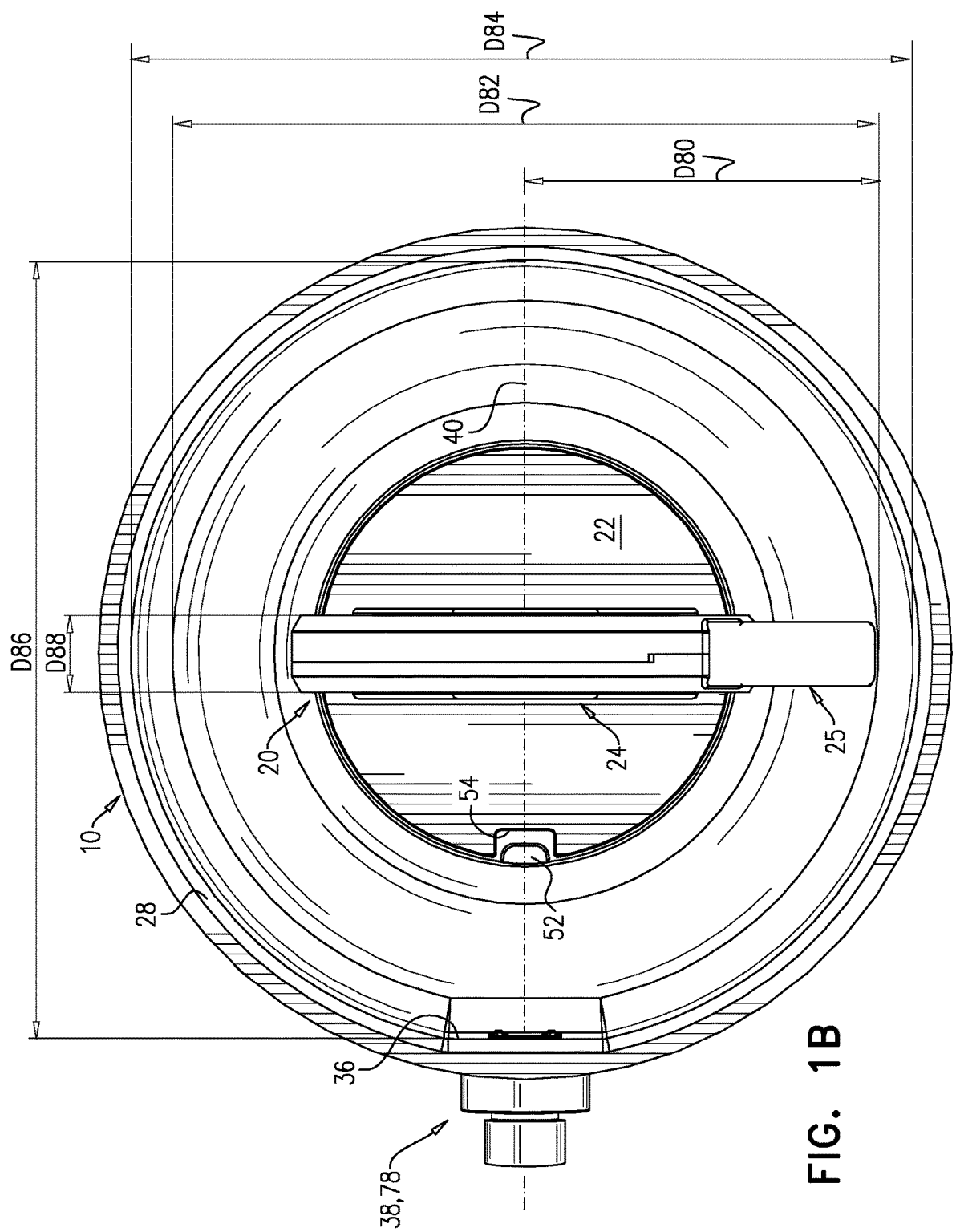
Figure 1C:
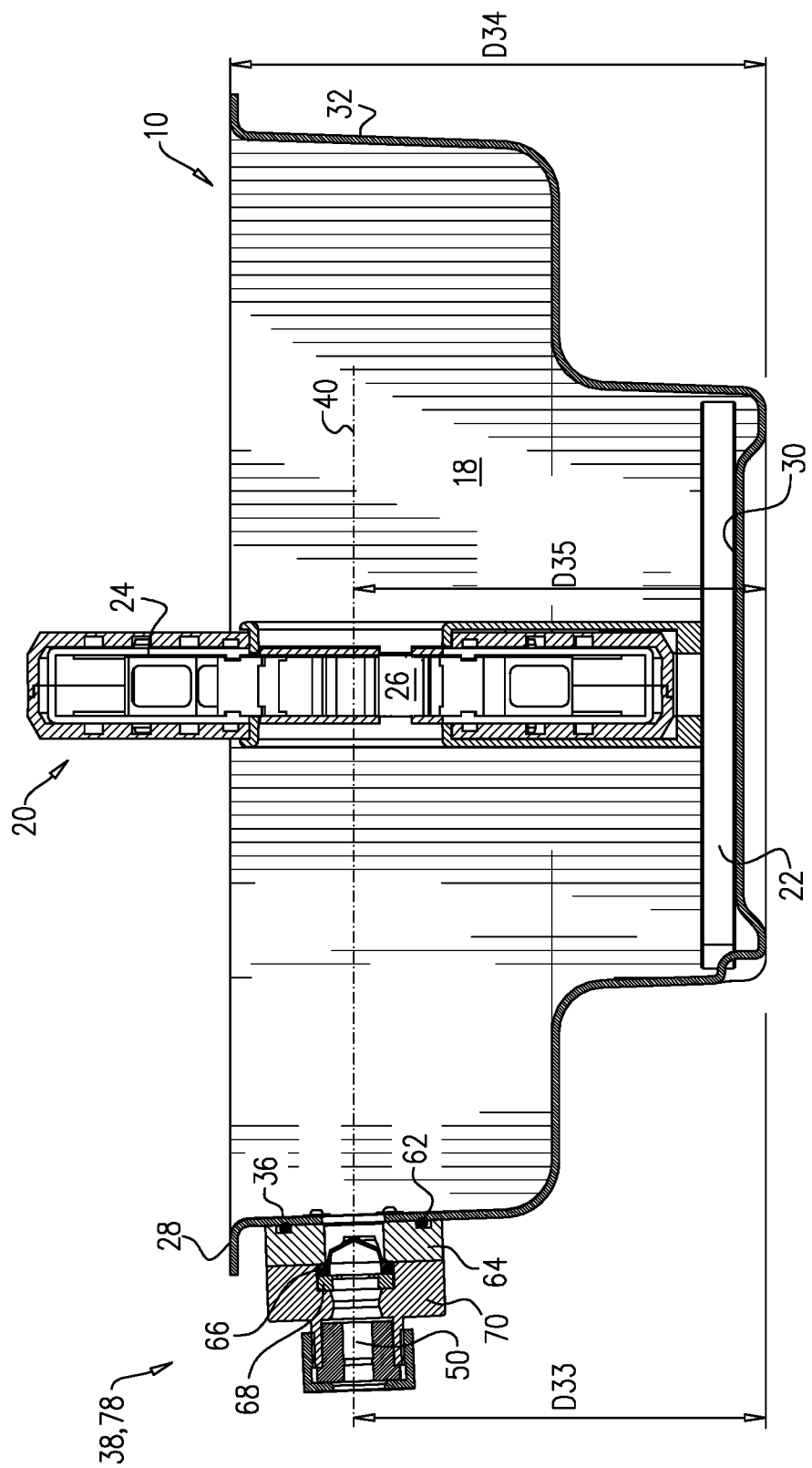

Reference is made to FIGS. 1A-C, which are schematic illustrations of a crimping assembly 10, comprising a crimping device 20 and a bath 28, in accordance with some applications of the invention.

Figure 2A:
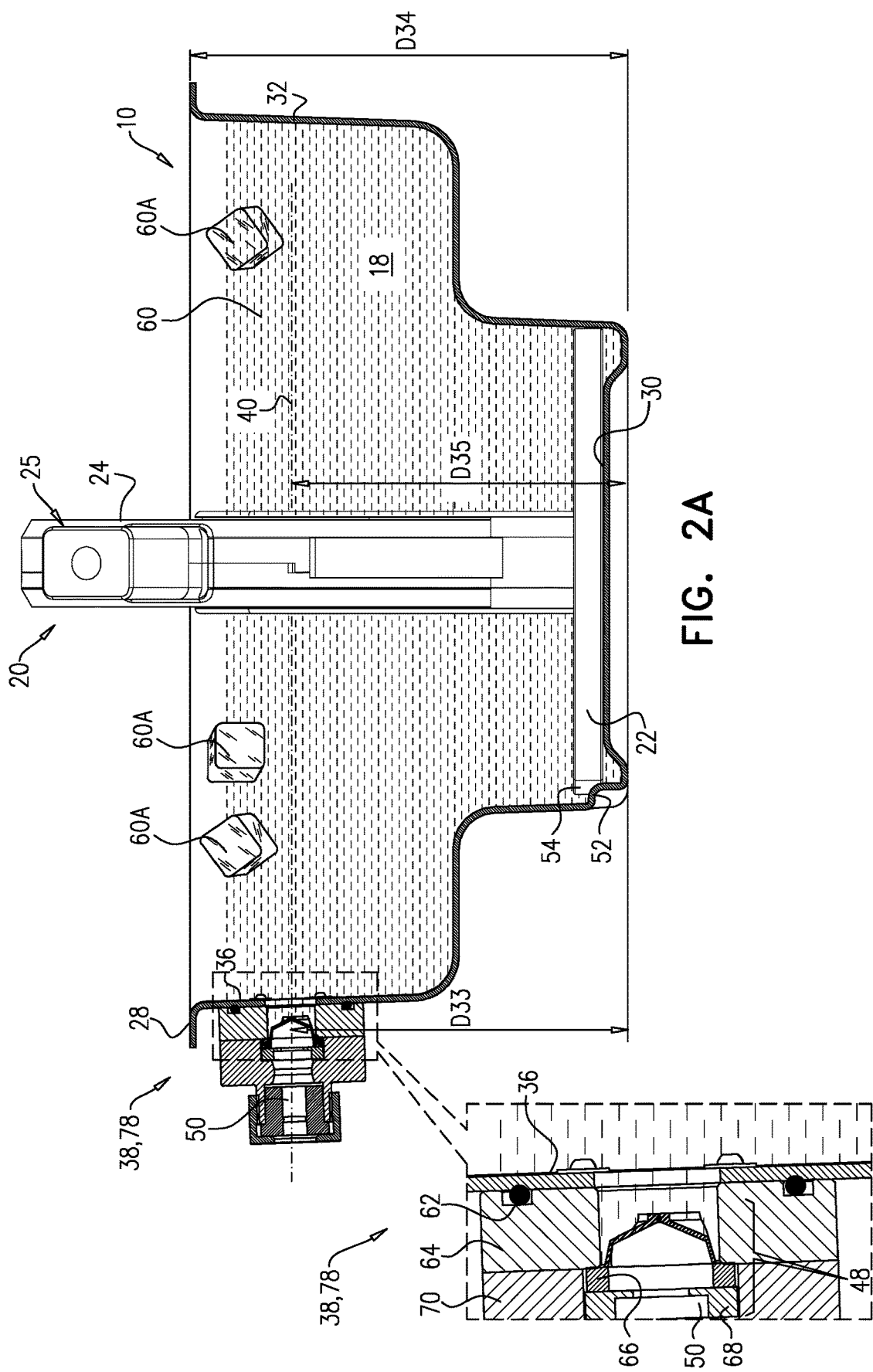
Figure 2B:
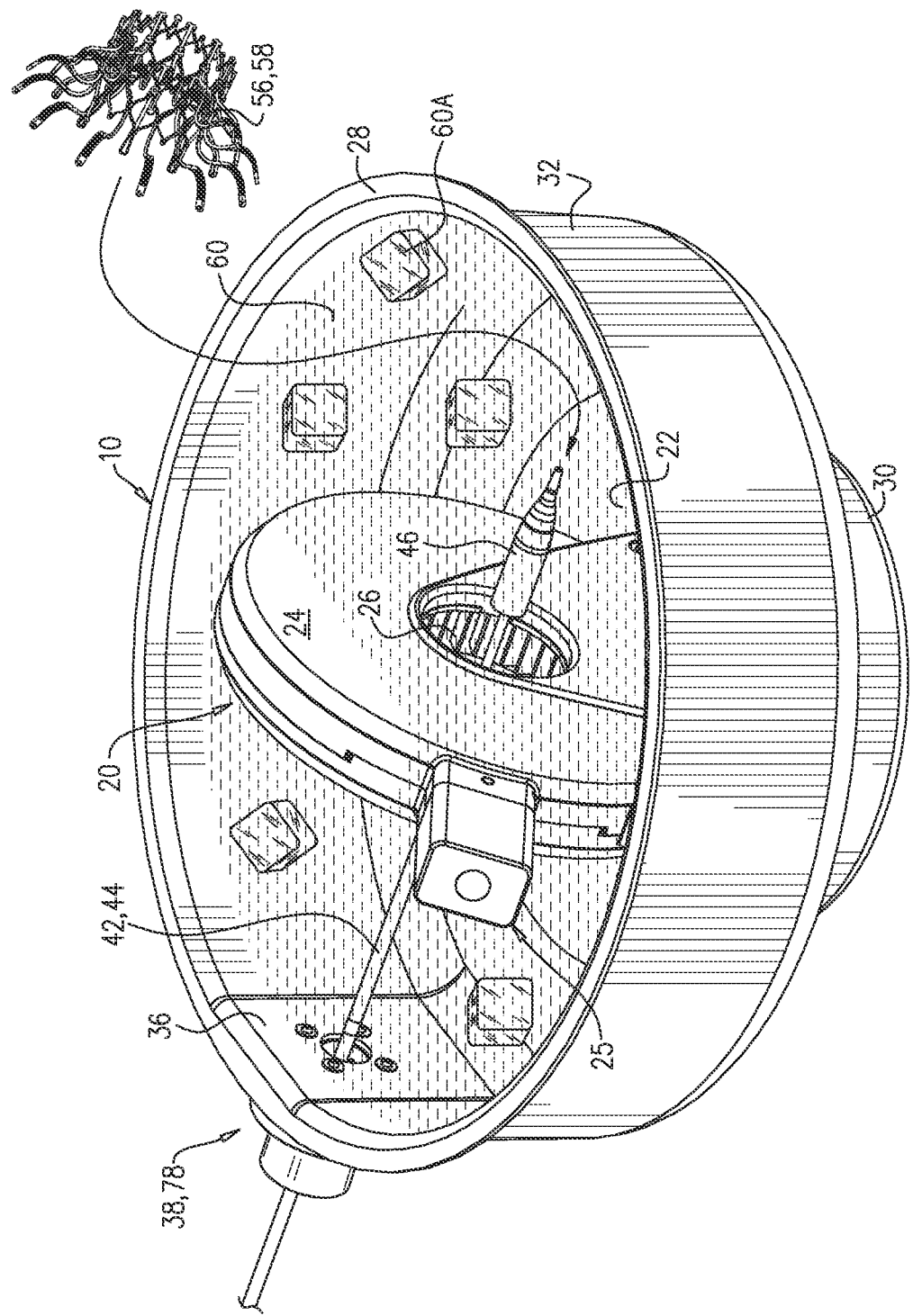
Figure 2C:
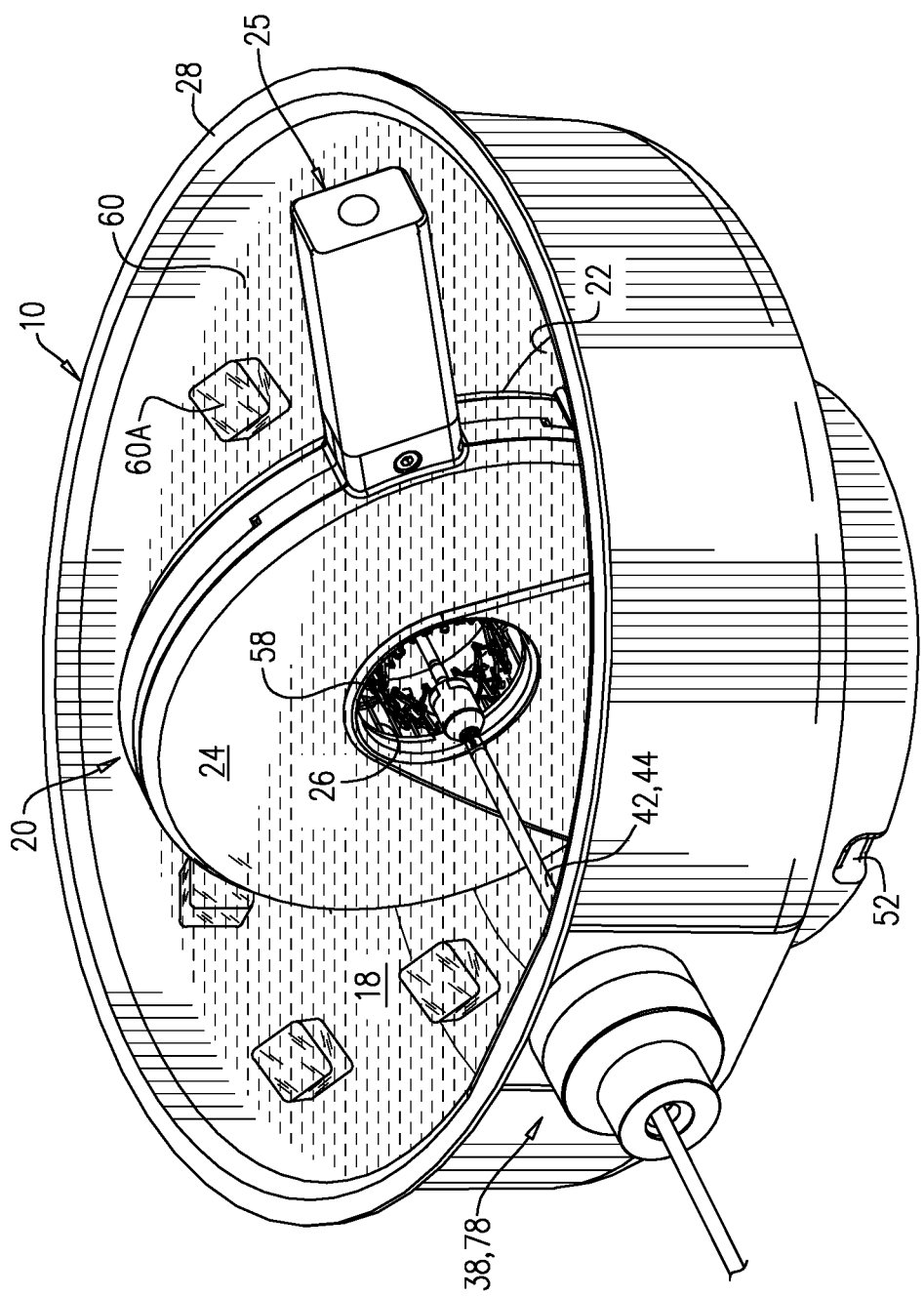
Figure 2D:
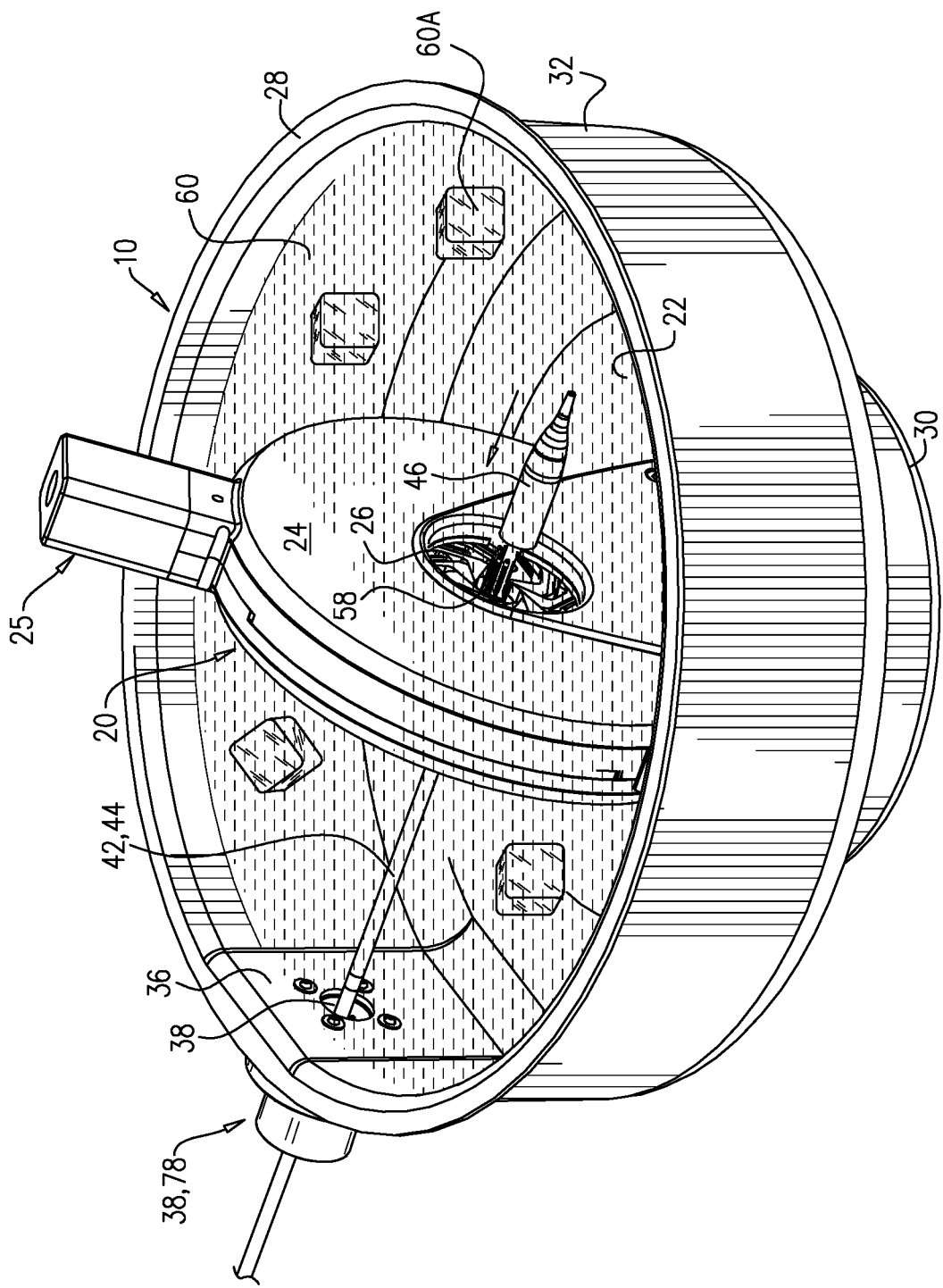
Figure 6A:
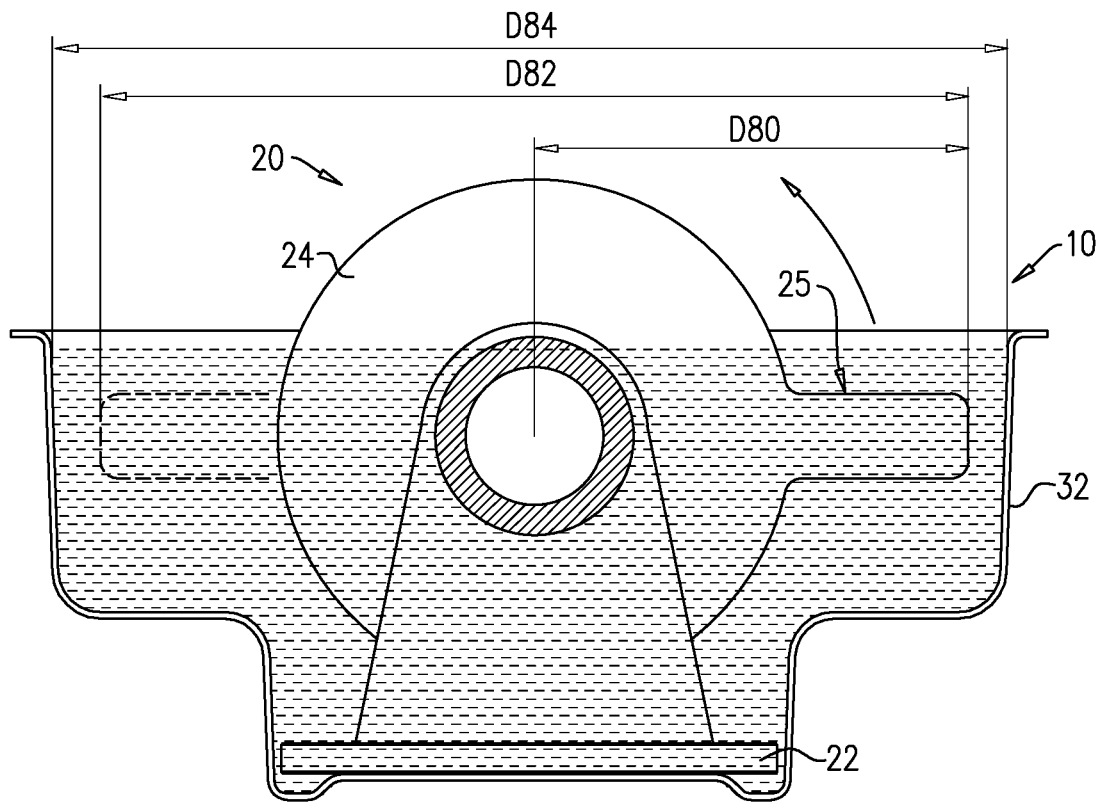
FIGS. 6A-B are schematic illustrations showing use of the crimping device disposed within the bath, in accordance with some applications of the invention.
Figure 6B:
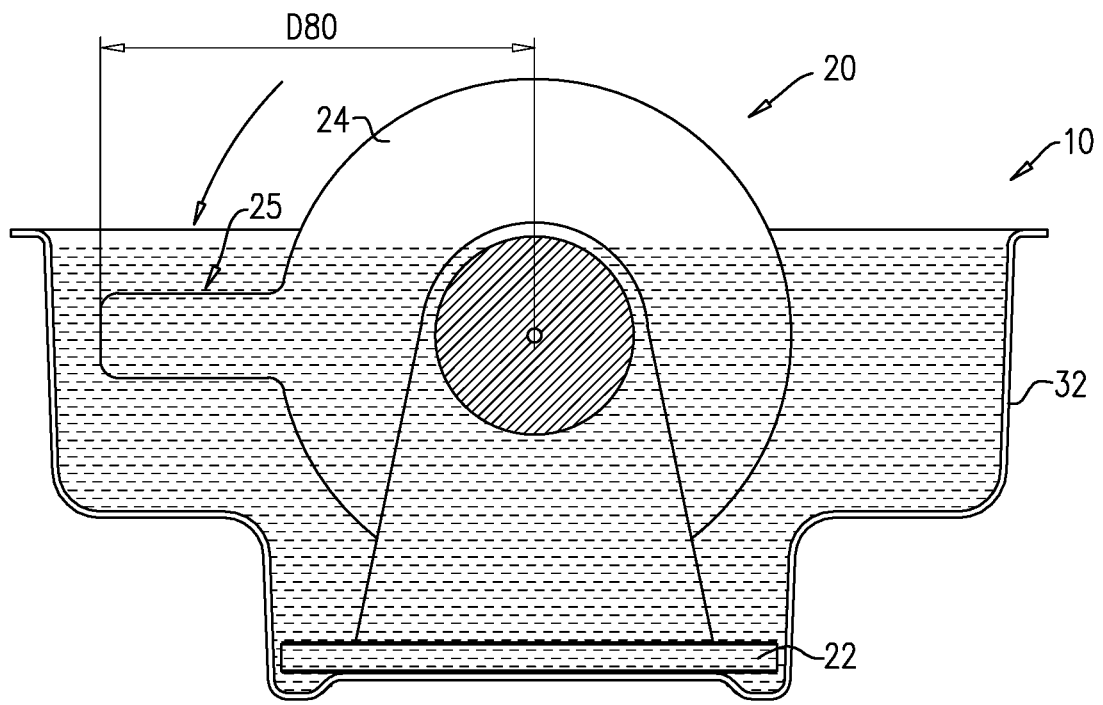

Crimping device 20 comprises a base 22, and a crimping mechanism 24 that defines a crimping aperture 26 having an open state shown in FIGS. 2B, 2C & 6A, as well as a narrowed state shown in FIGS. 2D and 6B. Bath 28 has a floor 30, and one or more side-walls 32 extending upward from the floor to a side-wall height D34. Typically, side-wall height D34 is the height to which bath 28 is fillable with a liquid, e.g., the lowest height of the one or more side-walls. Bath 28 defines a receptacle 18 that is shaped to receive a portion of crimping device 20, such that the crimping device is held securely by the bath 28.

FIGS. 1A-2E show crimping assembly 10 in its assembled state, in which crimping device 20 is disposed within bath 28, and is held securely by the bath. In the assembled state, the aperture 26 is below side-wall height D34. Typically, and as shown, the receptacle 18 is a recess in floor 30 of bath 28, and the recess is shaped to snugly receive base 22 of crimping device 20.

Typically, and as shown, bath 28 includes a port-defining side-wall 36, which defines a port 38 that defines a channel 50 between outside of the bath and inside of the bath. Typically, in the assembled state port 38 is aligned with crimping aperture 26. For example, a height D35 of the aperture may be within 1 cm of a height D33 of the port. Alternatively or additionally, port 38 may be disposed in a rotational position of the aperture that is within 5 degrees of a rotational position of the port 38. This alignment typically places channel 50 and aperture 26 along a co-linear axis 40 (FIG. 1A).

For some applications, crimping assembly 10 comprises two or more separable components, which undergo assembly prior to use. For example, bath 28 and crimping device 20 may be provided as separate components, which are assembled prior to use, e.g., by the operator or by a technician. For such applications, assembly 10 is typically assembled by introducing a portion of the crimping device (e.g., base 22) into receptacle 18 (FIG. 1A).

Typically, and as shown, bath 28 is shaped to receive crimping device 20 in a pre-defined rotational orientation of the crimping device with respect to the bath, and receptacle 18 and the portion of the crimping device (e.g., base 22) are cooperatively shaped to inhibit, in the assembled state, rotation of the crimping device 20 from the pre-defined rotational orientation. For example, and as shown, receptacle 18 may define a protrusion 52, and device 20 (e.g., base 22 thereof) may be shaped to define a notch 54 (or vice versa), the protrusion being disposed within the notch.

It is to be noted that the scope of the invention includes the use of other features to securely hold crimping device 20 within bath 28. For example, complementary couplings such as catches and/or locks may be used.

For other applications, crimping assembly 10 may be provided pre-assembled, with crimping device 20 already secured within bath 28. For some such applications, device 20 does not comprise a distinct base 22. Aside from these differences, the pre-assembled crimping assembly is typically as described hereinabove.

Reference is now also made to FIGS. 6A-B, which are schematic illustrations of crimping assembly 10, in accordance with some applications of the invention. Crimping mechanism 24 has a working radius D80 from the center of aperture 26 to the end of handle 25. For some applications, during the operation of crimping mechanism 24, handle 25 revolves about halfway circumferentially around mechanism 24 (i.e., with respect to aperture 26). Therefore, crimping mechanism 24 defines a working diameter D82, defined as twice working radius D80.

Bath 28 has an internal width D84, measured at height D33, typically transverse to axis 40. Typically, and as shown in FIG. 1B, internal width D84 is greater than working diameter D82. Typically, D84 is less than 10 cm greater than D82, (e.g., less than 5 cm greater, less than 2 cm greater, e.g., 1-10 mm greater).

Crimping mechanism 24 has a thickness D88. Thickness D88 is typically 2-5 cm (e.g., 2-3 cm). Typically, and as shown in FIG. 1B, bath 28 has another internal width D86, measured at height D33, measured along axis 40. For some applications, width D86 is sufficiently great that an operator may place a hand on each side of crimping mechanism 24 in order to load the implant onto the tool. Therefore, for some applications, width D86 is greater than thickness D88 plus 8-15 cm (e.g., 10-15 cm) on each side of crimping mechanism 24. Internal widths D84 and D88 are both typically 20-40 cm (e.g., 25-35 cm). For some applications, and as shown, bath 28 is generally circular, and diameters D84 and D88 are generally equal to each other (e.g., within 10 percent of each other, such as identical to each other).

Reference is made to FIGS. 2A-E, which are schematic illustrations showing crimping assembly 10 being used in combination with a delivery tool 42 to crimp a frame 56 of an implant 58, in accordance with some applications of the invention. As shown, implant 58 (FIG. 2B) may comprise a prosthetic heart valve, to be implanted at a native heart valve of a subject. Frame 56 is typically a shape-memory alloy such as nickel titanium (Nitinol). When an SMA device, in its original shape and size, is cooled to its martensitic state, and subsequently deformed, it will retain its deformed shape and size. Upon warming of the SMA device to its austenitic state, the device will return to its original shape and size.

As depicted in FIG. 2A, the co-linear axis 40 of port 38 and crimping aperture 26 enables advancement of a delivery tool 42 (FIG. 2B), which as depicted may include a shaft 44 and housing 46, through port 38, at least until housing 46 reaches aperture 26. Port 38 typically comprises an external portion 78 that is outside the bath. In certain embodiments, port 38 defines channel 50 having an internal diameter of 6-15 mm (e.g., 6-10 mm or 10-15 mm), and comprises a seal 48 that reversibly closes the channel (detailed in FIG. 2E) configured to maintain sealing as housing 46 and shaft 44 pass through channel 50 during the advancing.

The presence of a cooled liquid 60 within bath 28 maintains frame 56 at a cool temperature during crimping of the frame. Liquid 60 typically has a temperature of between −2 and 12 degrees C. (e.g., 4-10 degrees C.). In some applications of the invention, a portion 61 of liquid 60 may be frozen. For example, as well as putting liquid 60 into bath 28, frozen liquid (e.g., saline ice) 60a may also be added, in order to maintain liquid 60 at its cool temperature throughout the duration of the crimping of frame 56.

FIG. 2A shows assembly 10 prior to introduction of tool 42 or implant 58. FIG. 2A shows liquid 60 having been introduced into bath 28 prior to insertion of tool 42, but the liquid may alternatively be introduced after insertion of the tool. FIGS. 2B and 2C depict advancement of tool 42 into crimping aperture 26, such that frame 56 is disposed within the crimping aperture and immersed within cooled liquid 60. Frame 56 may be allowed to cool for a period of time while immersed in cooled liquid 60, prior to crimping. This period of time may typically last greater than 10 seconds (e.g., greater than 30 seconds) and/or less than 10 minutes (e.g., between 30 seconds and 10 minutes, such as 2-10 minutes). FIG. 2D shows contraction of crimping aperture 26 upon frame 56, crimping frame 56 while immersed in cooled liquid 60. Since implants comprising SMAs such as Nitinol are more easily deformed while in their martensitic state, it is therefore desirable to crimp such an implant while cooled below its transition temperature. Cooling of an SMA implant during crimping, which reduces a likelihood of damaging the implant or delivery tool during the crimping and loading processes, is achieved by disposition of crimping device 20 within a bath of the cooled liquid as shown in FIGS. 2C and 2D. FIG. 2E shows retraction of tool 42 through channel 50 of port 38, with implant 58 disposed within housing 46. Enlarged inset of FIG. 2E shows passage of tool shaft 44 through seal 48, while the seal prevents leakage of cooled liquid 60.

It is likely that some of liquid 60 becomes introduced into the subject during implantation of implant 58. Therefore, liquid 60 is typically suitable for introduction into the subject, e.g., being sterile, non-toxic, and/or isotonic. For example, liquid 60 may be sterile saline. It is to be noted that the crimping of implant 58 while immersed in cooled liquid 60, as described above, may reduce or obviate the need for subsequent flushing of air from the implant.

It is to be noted that the "heights" described herein (e.g., side-wall height D34, port-height D33, and aperture-height D35) are all heights above the same reference point, e.g., floor 30.

Reference is made to FIGS. 3, 4A-E, and 5, which are schematic illustrations showing the sealing of port 38 during advancing of housing 46 and shaft 44 of delivery tool 42 through the port. Some embodiments of the device include one or more washers 62, 66, and 68 fitted a first sealing nut 64 and a second sealing nut 70 (FIG. 3). Port 38 may be secured to port-defining side-wall 36 using screws (e.g., as shown), an adhesive, and/or any other suitable securing means.

Figure 4A:
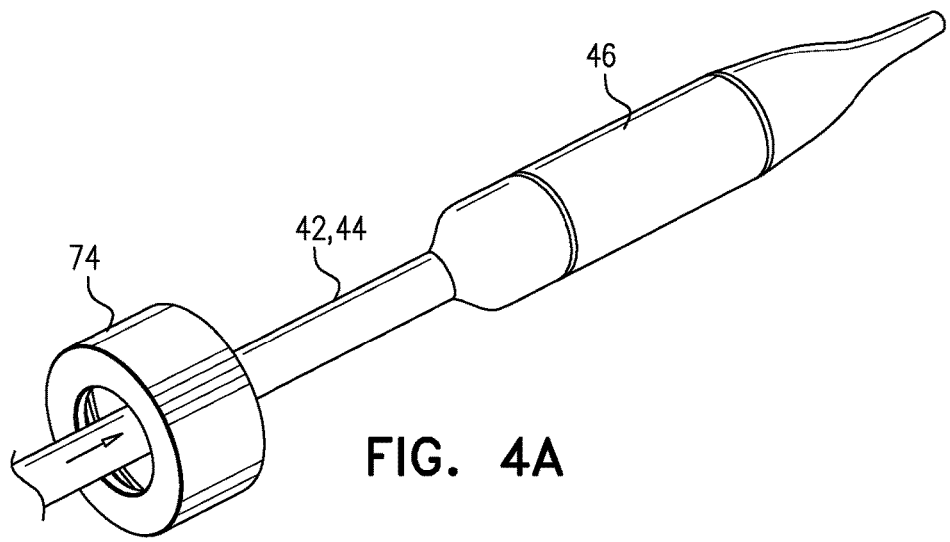
FIGS. 4A-E are schematic illustrations showing the use of a delivery tool with a cap, the port, and a plurality of plugs, in accordance with some applications of the invention.
Figure 4B:
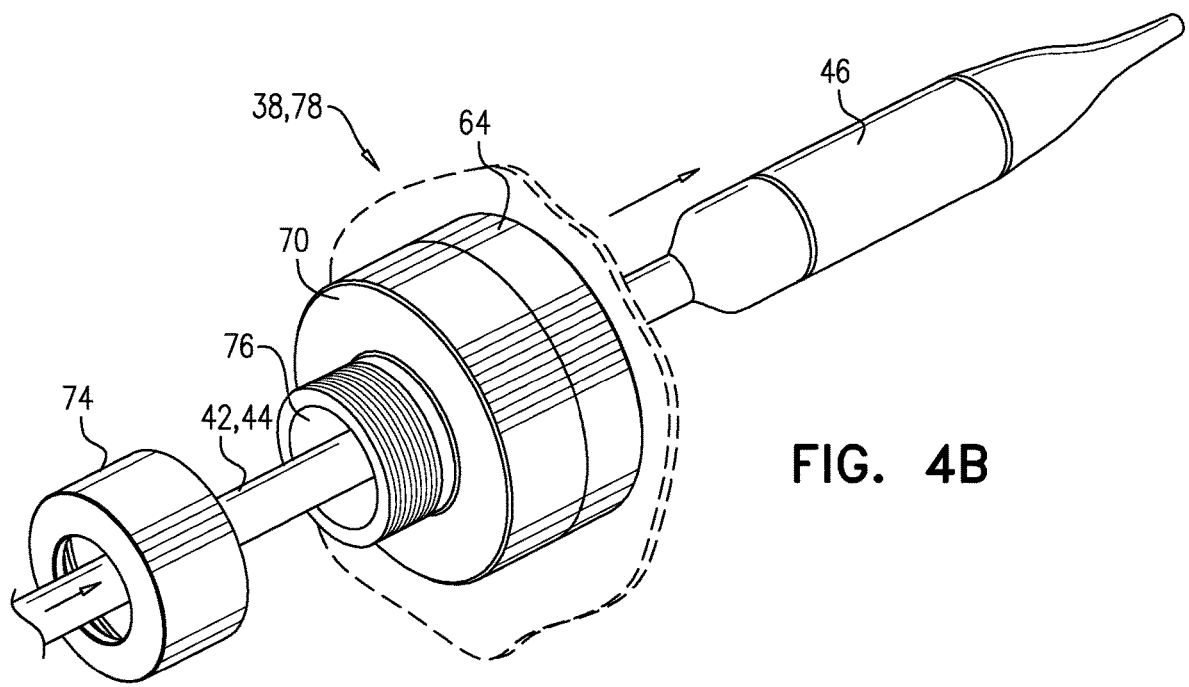
Figure 4C:
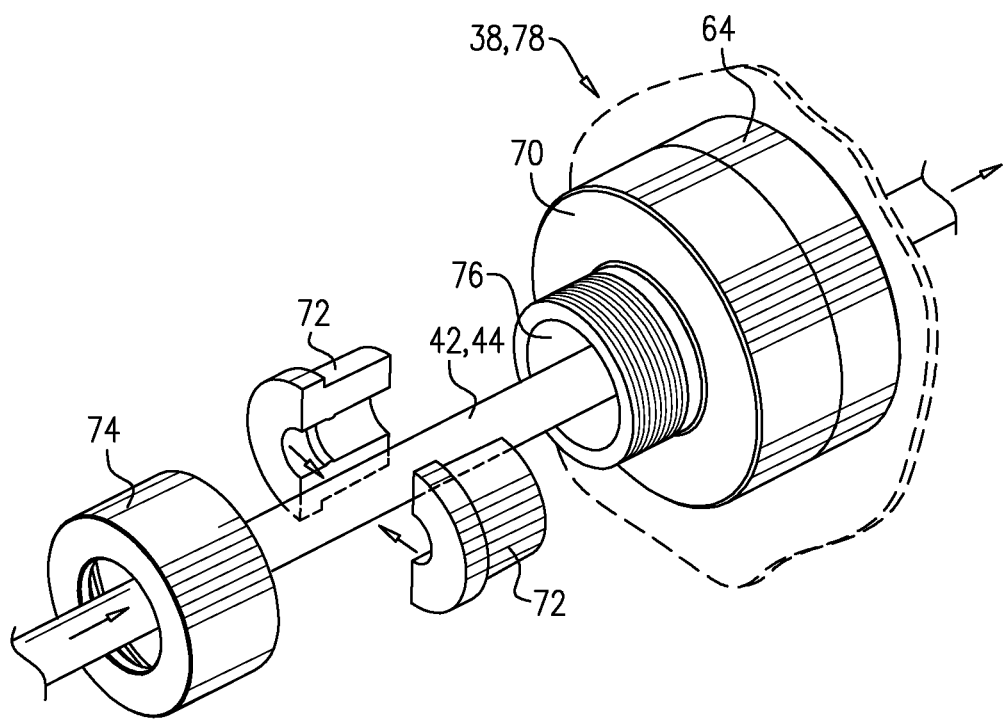
Figure 4D:
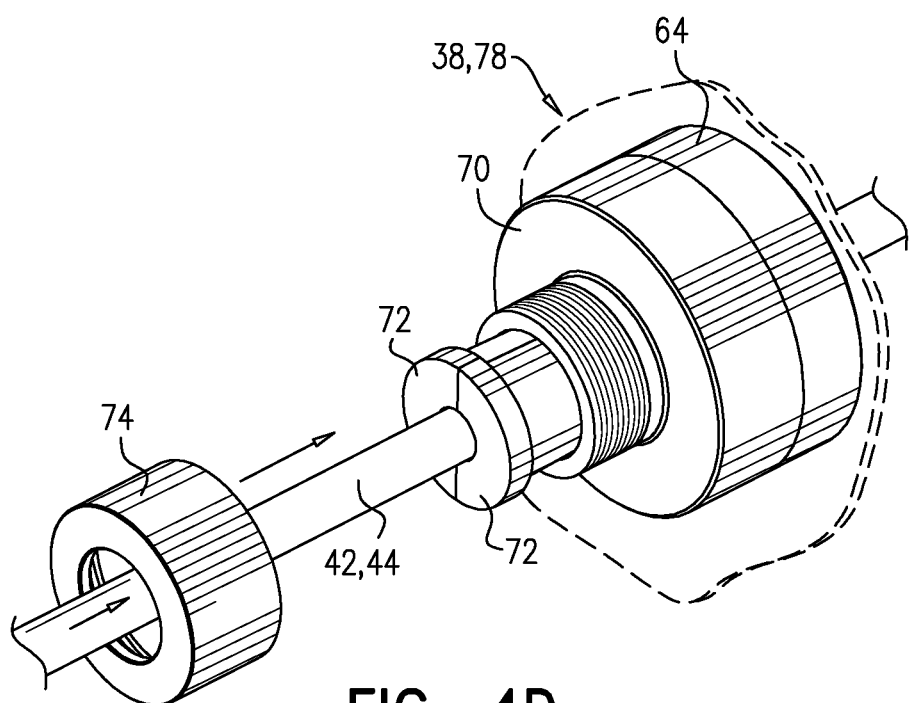

Delivery tool housing 46 is advanced through a cap 74 (i.e., through an opening defined in the cap) (FIG. 4A). Subsequently, housing 46 is advanced through port 38 (FIG. 4B). Optionally, a plurality of plugs 72 are subsequently arranged into a ring that circumscribes shaft 44 and is disposed in an annular gap 76 between the shaft and external portion 78 of port 38 (FIGS. 4C-D).

Figure 4E:
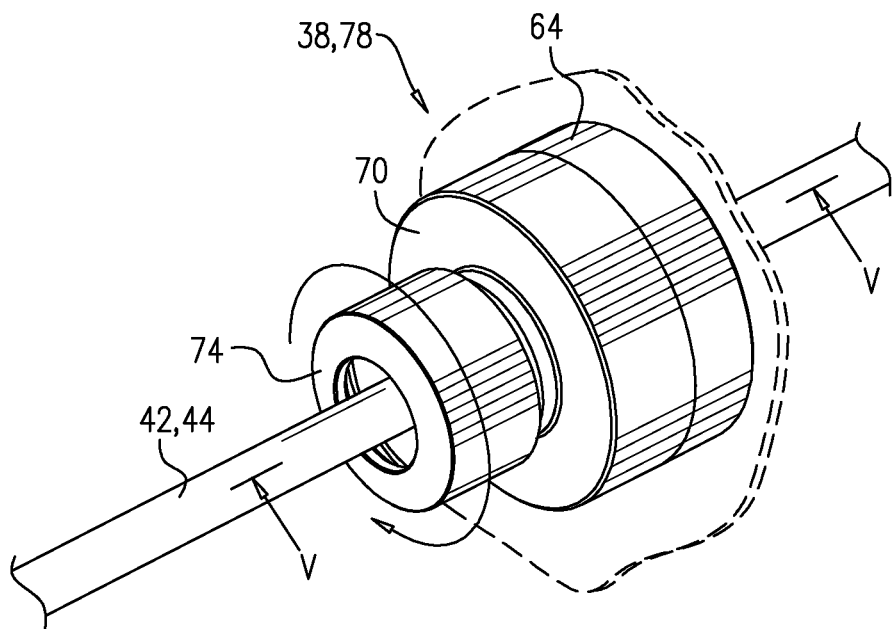
Figure 5:
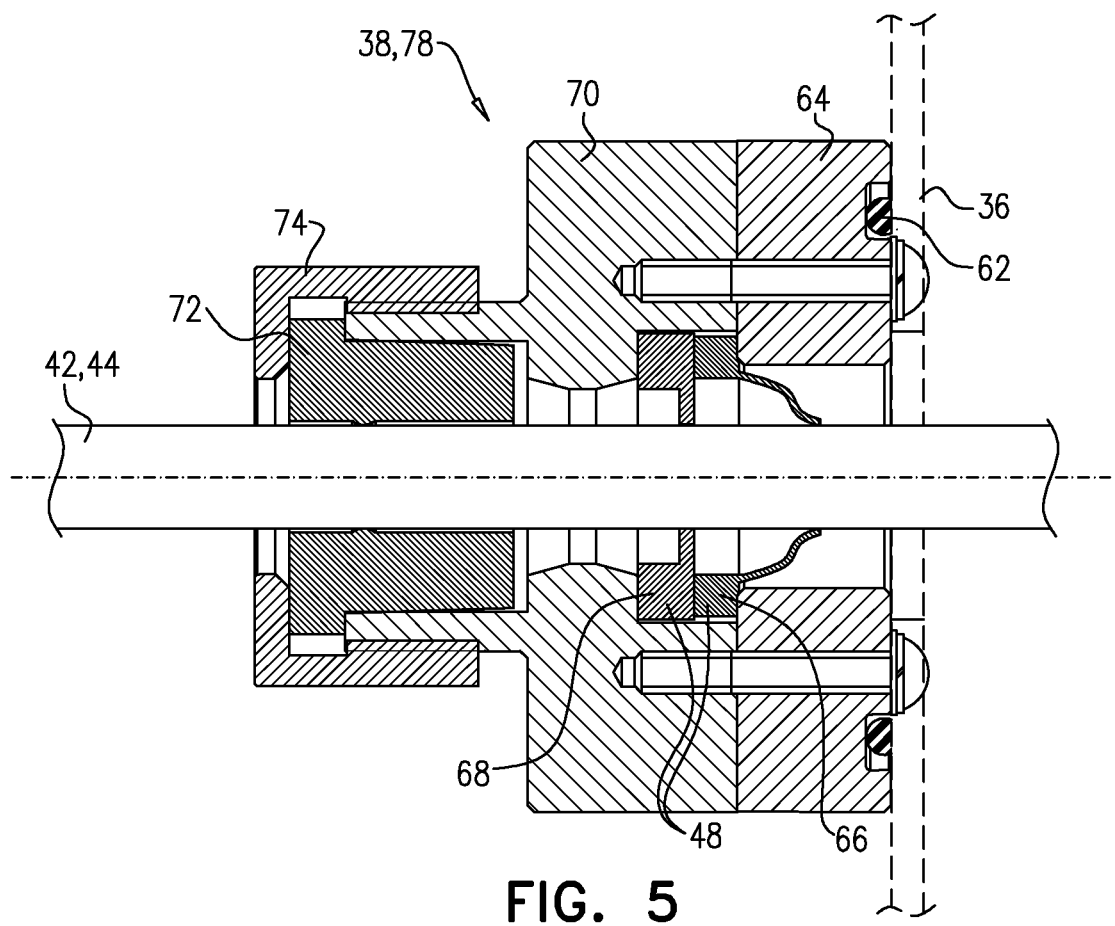
FIG. 5 is a schematic illustration showing sealing of the port around a delivery tool shaft, in accordance with some applications of the invention.

Subsequently, cap 74 is fastened to external portion 78 of port 38 (FIG. 4E). For example, for some applications, an interior portion of cap 74 may be shaped to define threading, and cap 74 may be secured to port 38 by being screwed onto the port. Using cap 74 and plugs 72 in this manner allows port 38 to be configured to facilitate advancement of tool 42 through the port with relatively low resistance, and for sealing of the port 38 to be subsequently increased using the cap and plugs.

For some applications, the screwing of cap 74 onto external portion 78 pushes plugs 72 into gap 76.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for crimping a frame of an implant, the apparatus comprising:
  a crimping device comprising (i) a base, and (ii) a crimping mechanism that defines a crimping aperture; and
  a bath (i) having a floor, (ii) defining a receptacle that is shaped to receive a portion of the crimping device, and (iii) having one or more side-walls, the one or more side-walls:
    extending upward from the floor to a side-wall height, and including a port-defining side-wall, wherein the port-defining side-wall defines a port between outside of the bath and inside of the bath;
the apparatus having an assembled state in which:
the portion of the crimping device has been received by the receptacle,
the crimping device is held securely by the bath,
the aperture is below the side-wall height, and
the port is aligned with the crimping aperture,
wherein:
the crimping aperture has an open state and a narrowed state,
the crimping device further comprises a handle, the crimping mechanism being actuatable by moving the handle circumferentially around the crimping mechanism, and
actuation of the crimping mechanism transitions the crimping aperture from its open state to its narrowed state.

2. The apparatus according to claim 1, wherein:
the crimping mechanism has a first side and a second side, and
the bath has an internal width sufficient to allow a human operator to simultaneously place a first hand inside the bath on the first side of the crimping mechanism, and a second hand inside the bath on the second side of the crimping mechanism.

3. The apparatus according to claim 1, wherein, in the assembled state, a height of the aperture is within 1 cm of a height of the port.

4. The apparatus according to claim 1, wherein the receptacle is a recess, configured to snugly receive the portion of the crimping device.

5. The apparatus according to claim 4, wherein the bath defines the recess in the floor, and the recess is shaped to receive at least a portion of the base.

6. The apparatus according to claim 1, wherein the bath is shaped to receive the crimping device in a pre-defined rotational orientation of the crimping device with respect to the bath.

7. The apparatus according to claim 6, wherein the receptacle and the portion of the crimping device are cooperatively shaped to inhibit, in the assembled state, rotation of the crimping device out of the pre-defined rotational orientation.

8. The apparatus according to claim 1, wherein the port defines a channel, and comprises a seal that reversibly closes the channel.

9. The apparatus according to claim 1, wherein:
the crimping device has a working diameter, defined between a first position of an end of the handle when the crimping aperture is in its open state, and a second position of the end of the handle when the aperture is in its narrowed state, and
the bath has an internal width that is greater than the working diameter.

10. The apparatus according to claim 9, wherein the internal width of the bath is less than 5 cm greater than the working diameter of the crimping device.

11. Apparatus for crimping a frame of an implant, the apparatus comprising:
a crimping device comprising (i) a base, and (ii) a crimping mechanism that defines a crimping aperture; and
a bath (i) having a floor, (ii) defining a receptacle that is shaped to receive a portion of the crimping device, and (iii) having one or more side-walls, the one or more side-walls:
extending upward from the floor to a side-wall height, and
including a port-defining side-wall, wherein the port-defining side-wall defines a port between outside of the bath and inside of the bath;
the apparatus having an assembled state in which:
the portion of the crimping device has been received by the receptacle,
the crimping device is held securely by the bath,
the aperture is below the side-wall height, and
the port is aligned with the crimping aperture,
wherein the crimping mechanism has a thickness, and wherein the bath has an internal width that is 16-24 cm greater than the thickness of the crimping mechanism.

12. Apparatus for crimping a frame of an implant, the apparatus comprising:
a crimping device comprising (i) a base, and (ii) a crimping mechanism that defines a crimping aperture; and
a bath (i) having a floor, (ii) defining a receptacle that is shaped to receive a portion of the crimping device, and (iii) having one or more side-walls, the one or more side-walls:
extending upward from the floor to a side-wall height, and
including a port-defining side-wall, wherein the port-defining side-wall defines a port between outside of the bath and inside of the bath;
the apparatus having an assembled state in which:
the portion of the crimping device has been received by the receptacle,
the crimping device is held securely by the bath,
the aperture is below the side-wall height, and
the port is aligned with the crimping aperture,
wherein:
the port defines a channel, and comprises a seal that reversibly closes the channel, and
the channel has an internal diameter of 6-15 mm.

13. Apparatus for crimping a frame of an implant, the apparatus comprising:
a crimping device comprising (i) a base, and (ii) a crimping mechanism that defines a crimping aperture;
a bath (i) having a floor, (ii) defining a receptacle that is shaped to receive a portion of the crimping device, and (iii) having one or more side-walls, the one or more side-walls:
extending upward from the floor to a side-wall height, and
including a port-defining side-wall, wherein the port-defining side-wall defines a port between outside of the bath and inside of the bath;
the apparatus having an assembled state in which:
the portion of the crimping device has been received by the receptacle,
the crimping device is held securely by the bath,
the aperture is below the side-wall height, and
the port is aligned with the crimping aperture, and
the port defines a channel, and comprises a seal that reversibly closes the channel; and
a delivery tool that comprises a shaft and a housing at a distal end of the shaft, the delivery tool being advanceable, housing-first, through the port, at least until the housing reaches the aperture, and wherein the seal is configured to maintain sealing as the housing and the shaft pass through the port during the advancing, wherein:

the port comprises an external portion outside of the bath, the external portion of the port is dimensioned such that, while the shaft extends through the port, an annular gap is defined around the shaft, between the shaft and the external portion of the port, the apparatus further comprises a cap and a plurality of plugs, the cap (i) defines an opening through which the housing is advanceable, and (ii) is securable to the external portion of the port, the plurality of plugs are shaped to be formable into a ring that circumscribes the shaft, and that fits snugly within the gap.

14. The apparatus according to claim 13, wherein the external portion of the port defines a screw thread, the cap defines a complementary screw thread, and the cap is securable to the external portion of the port by being screwed onto the external portion of the port.

15. A method for crimping an expandable frame, the method comprising:

introducing a cooled liquid into a bath, the bath having a floor and one or more side-walls, at least one of the side-walls being a port-defining side-wall that defines a port from inside the bath to outside the bath;

inserting at least a part of a delivery tool through the port into the bath, inserting the expandable frame, disposed on the part of the delivery tool, to a crimping aperture of a crimping mechanism disposed within and coupled to the bath; and while (i) the frame remains disposed within the aperture, and (ii) the frame is at least partially submerged in the liquid, crimping the frame onto the delivery tool by actuating the crimping mechanism, wherein actuating the crimping mechanism comprises revolving a handle about halfway circumferentially around the crimping mechanism, wherein revolving the handle causes transitioning of the crimping aperture from an open state to a narrowed state.

16. The method according to claim 15, further comprising introducing, into the bath, a frozen portion of the liquid.

17. The method according to claim 15, further comprising, prior to crimping the frame, immersing the frame in the cooled liquid in the bath for between 30 seconds and 10 minutes.

18. The method according to claim 15, further comprising forming a crimping assembly in which the crimping mechanism is held securely within the bath, and the crimping aperture is below the side-wall height, by placing the crimping device into the bath, and coupling the crimping device to the bath.

19. The method according to claim 18, wherein forming the crimping assembly comprises coupling the crimping device to the bath such that the port is aligned with the aperture.

20. A method for crimping an expandable frame, the method comprising:

introducing a cooled liquid into a bath, the bath having a floor and one or more side-walls, at least one of the side-walls being a port-defining side-wall that defines a port from inside the bath to outside the bath;

inserting at least a part of a delivery tool through the port into the bath, inserting the expandable frame, disposed on the part of the delivery tool, to a crimping aperture of a crimping mechanism disposed within and coupled to the bath; and while (i) the frame remains disposed within the aperture, and (ii) the frame is at least partially submerged in the liquid, crimping the frame onto the delivery tool by actuating the crimping mechanism, wherein the crimping mechanism has a first side and a second side, and wherein inserting the expandable frame comprises manually inserting the frame to within the crimping aperture facilitated by placing a first hand within the bath on the first side of the crimping mechanism, and a second hand within the bath on the second side of the crimping mechanism.

21. A method for crimping an expandable frame, the method comprising:

introducing a cooled liquid into a bath, the bath having a floor and one or more side-walls, at least one of the side-walls being a port-defining side-wall that defines a port from inside the bath to outside the bath;

inserting at least a part of a delivery tool through the port into the bath, inserting the expandable frame, disposed on the part of the delivery tool, to a crimping aperture of a crimping mechanism disposed within and coupled to the bath; and while (i) the frame remains disposed within the aperture, and (ii) the frame is at least partially submerged in the liquid, crimping the frame onto the delivery tool by actuating the crimping mechanism, wherein the port includes an external portion outside of the bath, and wherein the method further comprises:

prior to inserting the part of the delivery tool through the port into the bath, passing the part of the delivery tool through a cap; and subsequently to inserting the part of the delivery tool through the port into the bath, fastening the cap to the external portion of the port.

22. The method according to claim 21, wherein:

the delivery tool includes a shaft, inserting at least the part of the delivery tool through the port into the bath comprises positioning the shaft through the port, the method further comprises, prior to securing the cap to the external portion of the port, arranging a plurality of plugs into a ring that circumscribes the shaft and is disposed in a gap between the shaft and the external portion of the port, and fastening the cap to the external portion of the port comprises securing the ring of plugs within the gap.

23. The method according to claim 22, wherein fastening the cap to the external portion of the port comprises screwing the cap onto the external portion of the port, sealing the port.

24. The method according to claim 23, wherein screwing the cap onto the external portion of the port further comprises pushing the plurality of plugs into the gap between the shaft and the external portion of the port.

25. The method according to claim 15, further comprising coupling the frame to the part of the delivery tool.

26. The method according to claim 25, wherein coupling the frame onto the part of the delivery tool comprises coupling the frame to the part of the delivery tool subsequently to inserting the part of the delivery tool through the port into the bath.

* * * * *